US010960056B2

(12) United States Patent
Kim et al.

(10) Patent No.: US 10,960,056 B2
(45) Date of Patent: Mar. 30, 2021

(54) ANTI-INFLAMMATORY PEPTIDES AND COMPOSITION COMPRISING THE SAME

(71) Applicants: GemVax & KAEL Co., Ltd., Daejeon (KR); Sang Jae Kim, Seoul (KR)

(72) Inventors: Sang Jae Kim, Seoul (KR); Kyung Hee Kim, Seoul (KR); Kyu-Yong Lee, Seoul (KR); Seong-Ho Koh, Seoul (KR); Hyun-Hee Park, Seoul (KR); Sung Jin Huh, Seoul (KR); Woo Jin Lee, Seoul (KR); Bum Joon Kim, Daejeon (KR)

(73) Assignee: GemVax & KAEL Co., Ltd., Daejeon (KR)

( * ) Notice: Subject to any disclaimer, the term of this patent is extended or adjusted under 35 U.S.C. 154(b) by 0 days.

(21) Appl. No.: 16/025,352

(22) Filed: Jul. 2, 2018

(65) Prior Publication Data
US 2019/0030137 A1 Jan. 31, 2019

Related U.S. Application Data

(62) Division of application No. 15/343,502, filed on Nov. 4, 2016, now Pat. No. 10,039,811, which is a division of application No. 14/400,291, filed as application No. PCT/EP2013/059460 on May 7, 2013, now Pat. No. 9,540,419.

(30) Foreign Application Priority Data

May 11, 2012 (KR) .................. 10-2012-0050529
May 11, 2012 (KR) .................. 10-2012-0050533
Jul. 2, 2012 (KR) .................. 10-2012-0071989
Sep. 19, 2012 (KR) .................. 10-2012-0104144
Sep. 19, 2012 (KR) .................. 10-2012-0104207
Mar. 15, 2013 (WO) ............... PCT/EP2013/055329

(51) Int. Cl.
A61K 38/45 (2006.01)
A61K 38/04 (2006.01)
A61K 38/10 (2006.01)
A61K 8/64 (2006.01)
A61Q 19/00 (2006.01)
C07K 7/08 (2006.01)
C12N 9/02 (2006.01)
C07K 14/47 (2006.01)
A23L 33/18 (2016.01)
A61K 38/00 (2006.01)

(52) U.S. Cl.
CPC .............. A61K 38/45 (2013.01); A23L 33/18 (2016.08); A61K 8/64 (2013.01); A61Q 19/00 (2013.01); C07K 7/08 (2013.01); C07K 14/4703 (2013.01); C12N 9/0069 (2013.01); C12N 9/0083 (2013.01); C12Y 113/11 (2013.01); C12Y 114/99001 (2013.01); C12Y 207/07049 (2013.01); A23V 2002/00 (2013.01); A61K 38/00 (2013.01); Y02A 50/30 (2018.01)

(58) Field of Classification Search
CPC .......... A61K 38/45; A61K 8/64; A61K 38/04; A61K 38/10; A61Q 19/00; C07K 14/4703; C07K 7/08
USPC .... 514/13.2, 16.4, 16.6, 17.8, 18.7, 1.5, 1.6, 514/1.7, 1.8, 21.4, 2.1, 4.3; 530/326
See application file for complete search history.

(56) References Cited

U.S. PATENT DOCUMENTS

| 6,967,211 | B2 | 11/2005 | Inoue |
| 7,030,211 | B1 | 4/2006 | Gaudernack et al. |
| 7,786,084 | B2 | 8/2010 | Benner et al. |
| 7,794,723 | B2 | 9/2010 | Gaudernack et al. |
| 8,828,403 | B2 | 9/2014 | Filaci et al. |
| 8,933,197 | B2 | 1/2015 | Bogin et al. |
| 9,023,987 | B2 | 5/2015 | Chung et al. |
| 9,540,419 | B2 | 1/2017 | Kim et al. |
| 9,572,858 | B2 | 2/2017 | Kim et al. |
| 10,039,811 | B2 | 8/2018 | Kim et al. |
| 2002/0042401 | A1 | 4/2002 | Ferguson et al. |
| 2003/0027769 | A1 | 2/2003 | Scialdone et al. |
| 2003/0143228 | A1 | 7/2003 | Chen et al. |

(Continued)

FOREIGN PATENT DOCUMENTS

| CN | 1313773 A | 9/2001 |
| EP | 1020190 A3 | 10/2000 |

(Continued)

OTHER PUBLICATIONS

Inflammatory disease list from Merck Manual, pp. 1-4. (Year: 2020).*

(Continued)

Primary Examiner — Julie Ha
(74) Attorney, Agent, or Firm — Clark & Elbing LLP

(57) ABSTRACT

A peptide with anti-inflammatory activity, wherein the peptide comprises SEQ ID NO: 1, the peptide has above 80% homology of amino acid with above-mentioned sequence, or the peptide is the fragment of the above-mentioned peptides is described. An anti-inflammatory composition comprising the above mentioned peptides is described. According to the present invention, a peptide comprising a sequence of SEQ ID NO: 1 has outstanding efficacy in both suppressing inflammation and in prophylactic means. Therefore, the composition comprising the peptide of this invention can be used as anti-inflammatory pharmaceutical composition or as cosmetic composition, in turn, treating and preventing a variety of different types of inflammatory diseases.

9 Claims, 11 Drawing Sheets
Specification includes a Sequence Listing.

(56) References Cited

U.S. PATENT DOCUMENTS

| | | |
|---|---|---|
| 2006/0106196 A1 | 5/2006 | Gaudernack et al. |
| 2007/0190561 A1 | 8/2007 | Morin et al. |
| 2008/0025986 A1 | 1/2008 | Ozes et al. |
| 2009/0136917 A1 | 5/2009 | Szalay et al. |
| 2009/0186802 A1 | 7/2009 | Alluis et al. |
| 2009/0215852 A1 | 8/2009 | Bascomb et al. |
| 2010/0003229 A1 | 1/2010 | Santos |
| 2011/0135692 A1 | 6/2011 | Filaci et al. |
| 2011/0150873 A1 | 6/2011 | Grainger |
| 2011/0183925 A1 | 7/2011 | Sato et al. |
| 2012/0065124 A1 | 3/2012 | Morishita et al. |
| 2012/0208755 A1 | 8/2012 | Leung |
| 2012/0277290 A1 | 11/2012 | Collard et al. |
| 2013/0129760 A1 | 5/2013 | Gaudernack et al. |
| 2013/0230591 A1 | 9/2013 | Fellous et al. |
| 2015/0099692 A1 | 4/2015 | Kim et al. |
| 2015/0099693 A1 | 4/2015 | Kim et al. |
| 2015/0175978 A1 | 6/2015 | Kim |
| 2015/0307859 A1 | 10/2015 | Kim |
| 2015/0343095 A1 | 12/2015 | Kim |
| 2015/0353903 A1 | 12/2015 | Kim |
| 2016/0002613 A1 | 1/2016 | Kim |
| 2016/0008438 A1 | 1/2016 | Kim |
| 2016/0082089 A1 | 3/2016 | Kim |
| 2016/0120966 A1 | 5/2016 | Kim |
| 2016/0137695 A1 | 5/2016 | Kim |
| 2016/0151512 A1 | 6/2016 | Kim |
| 2016/0250279 A1 | 9/2016 | Kim |
| 2016/0296604 A1 | 10/2016 | Kim |
| 2016/0375091 A1 | 12/2016 | Kim |
| 2017/0028035 A1 | 2/2017 | Kim |
| 2017/0058001 A1 | 3/2017 | Kim |
| 2017/0081376 A1 | 3/2017 | Kim et al. |
| 2017/0128557 A1 | 5/2017 | Kim et al. |
| 2017/0143806 A1 | 5/2017 | Kim et al. |
| 2017/0275603 A1 | 9/2017 | Kim et al. |
| 2017/0360870 A1 | 12/2017 | Kim |
| 2018/0036384 A1 | 2/2018 | Kim et al. |

FOREIGN PATENT DOCUMENTS

| | | |
|---|---|---|
| EP | 1093381 B2 | 7/2009 |
| EP | 1817337 B1 | 1/2011 |
| JP | 2002/520293 A | 7/2002 |
| JP | 2002520293 A | 7/2002 |
| JP | 2002522373 A | 7/2002 |
| JP | 2010252810 A | 11/2010 |
| JP | 2011515498 A | 5/2011 |
| JP | 2012500279 A | 1/2012 |
| JP | 2012526524 A | 11/2012 |
| JP | 5577472 B2 | 8/2014 |
| KR | 19930001915 A | 2/1993 |
| KR | 20010012613 A | 2/2001 |
| KR | 20010020601 A | 3/2001 |
| KR | 20040015087 A | 2/2004 |
| KR | 20040045400 A | 6/2004 |
| KR | 20040107492 A | 12/2004 |
| KR | 20050020987 A | 3/2005 |
| KR | 20050040517 A | 5/2005 |
| KR | 20060065588 A | 6/2006 |
| KR | 20060109903 A | 10/2006 |
| KR | 20070083218 A | 8/2007 |
| KR | 20080084818 A | 9/2008 |
| KR | 20090033878 A | 4/2009 |
| KR | 20090103957 A | 10/2009 |
| KR | 20100058541 A | 6/2010 |
| KR | 20100085527 A | 7/2010 |
| KR | 20110057049 A | 5/2011 |
| KR | 20110060940 A | 6/2011 |
| KR | 20110062943 A | 6/2011 |
| KR | 20110130943 A | 12/2011 |
| KR | 20120018188 A | 2/2012 |
| KR | 20120026408 A | 3/2012 |
| KR | 20120035150 A | 4/2012 |
| KR | 20120087885 A | 8/2012 |
| KR | 20120121196 A | 11/2012 |
| KR | 20120130996 A | 12/2012 |
| KR | 20120133661 A | 12/2012 |
| KR | 20130004949 A | 1/2013 |
| KR | 20130041896 A | 4/2013 |
| KR | 20140037698 A | 3/2014 |
| KR | 20140104288 A | 8/2014 |
| WO | WO-0002581 A1 | 1/2000 |
| WO | WO-0007565 A2 | 2/2000 |
| WO | WO 2009/025871 | 2/2009 |
| WO | WO-2009120914 A1 | 10/2009 |
| WO | WO-2010003520 A2 | 1/2010 |
| WO | WO-2010012850 A1 | 2/2010 |
| WO | WO-2010022125 A1 | 2/2010 |
| WO | WO-2010128807 A2 | 11/2010 |
| WO | WO-2011101173 A1 | 8/2011 |
| WO | WO-2011150494 A1 | 12/2011 |
| WO | WO-2013100500 A1 | 7/2013 |
| WO | WO-2013118899 A1 | 8/2013 |
| WO | WO-2013135266 A1 | 9/2013 |
| WO | WO-2013167298 A1 | 11/2013 |
| WO | WO-2013167574 A1 | 11/2013 |
| WO | WO-2013169060 A1 | 11/2013 |
| WO | WO-2013169067 A1 | 11/2013 |
| WO | WO-2013169077 A1 | 11/2013 |
| WO | WO-2014010971 A1 | 1/2014 |
| WO | WO-2014012683 A1 | 1/2014 |
| WO | WO-2014046478 A1 | 3/2014 |
| WO | WO-2014046481 A1 | 3/2014 |
| WO | WO-2014046490 A1 | 3/2014 |
| WO | WO-2014130909 A1 | 8/2014 |
| WO | WO-2014171792 A1 | 10/2014 |
| WO | WO-2014196841 A1 | 12/2014 |
| WO | WO-2014204281 A1 | 12/2014 |
| WO | WO-2015060673 A1 | 4/2015 |
| WO | WO-2015076621 A1 | 5/2015 |
| WO | WO-2015093854 A1 | 6/2015 |
| WO | WO-2015156649 A1 | 10/2015 |
| WO | WO-2015167067 A1 | 11/2015 |
| WO | WO-2016105086 A1 | 6/2016 |
| WO | WO-2016137162 A1 | 9/2016 |
| WO | WO-2017078440 A1 | 5/2017 |

OTHER PUBLICATIONS

Prostatitis from Merck Manual, pp. 1-7. (Year: 2020).*
Urogenital disease list from Merck Manual, pp. 1-3. (Year: 2020).*
JP2002520293 Machine Translation; pp. 1-25. Jul. 9, 2002 (Year: 2002).*
CN 1313773 Machine Translation, pp. 1-16, Sep. 19, 2001. (Year: 2001).*
Altschul, S.F., et al., "Basic Local Alignment Search Tool," Journal of Molecular Biology 215(3):403-410, Elsevier, England (1990).
Beer, T.M., et al., "Phase II Study of Weekly Docetaxel in Symptomatic Androgen-independent Prostate Cancer," Annals of Oncology 12(9):1273-1279, Oxford University Press, England (2001).
Bernhardt, S.L., et al., "Telomerase Peptide Vaccination of Patients with Non-Resectable Pancreatic Cancer: A Dose Escalating Phase I/II Study," British Journal of Cancer 95(11):1474-1482, Nature Publishing Group on behalf of Cancer Research, England (2006).
Bohonowych, J.E., et al., "Comparative Analysis of Novel and Conventional HSP90 Inhibitors on Hif Activity and Angiogenic Potential in Clear Cell Renal Cell Carcinoma: Implications for Clinical Evaluation," BMC Cancer 11:520, BioMed Central, England (2011).
Bonaldi, T., et al., "Monocytic Cells Hyperacetylate Chromatin Protein HMGB1 to Redirect it Towards Secretion," The EMBO Journal 22(20):5551-5560, Wiley Blackwell, England (2003).
Brandenburg, K., et al., "Peptide-based Treatment of Sepsis," Applied Microbiology and Biotechnology 90(3):799-808, Springer International, Germany (2011).
Bruns, A.F., et al., "A Heat-shock Protein Axis Regulates VEGFR2 Proteolysis, Blood Vessel Development and Repair," PloS One 7(11):e48539, Public Library of Science, United States (2012).
Brunsvig, P.F., et al., "Telomerase Peptide Vaccination in NSCLC: A Phase II Trial in Stage III Patients Vaccinated after Chemoradiotherapy

(56) References Cited

OTHER PUBLICATIONS and an 8-year Update on a Phase I/II Trial," Clinical Cancer Research 17(21):6847-6857, The Association, United States (2011).
Calderwood, S.K., et al., "Heat Shock Proteins in Cancer: Chaperones of Tumorigenesis," Trends in Biochemical Sciences 31(3):164-172, Elsevier Trends Journals, England (2006).
Cho, Y.J., "GemVax & Kael (082270)," Hana Daetoo Securities, Company Report, Sep. 10, 2012, 9 pages.
Choi, S.G., "Recent Advances in Cancer Cachexia," Journal of Korean Oncology Nursing 11(1):20-25 (2011).
Respiratory Diseases from Merck Manual, pp. 1-4. Accessed Nov. 2, 2017.
Nonallergic rhinitis from Merck Manual, pp. 1-4. Accessed Nov. 2, 2017.
Dahlgren, K.N., et al., "Oligomeric and Fibrillar Species of Amyloid-beta Peptides Differentially Affect Neuronal Viability," Journal of Biological Chemistry 277(35):32046-32053, American Society for Biochemistry and Molecular Biology, United States (2002).
Dementia from Merck Manual, accessed on Jul. 29, 2009, pp. 1-17.
Dempsey, N.C., et al., "Differential Heat Shock Protein Localization in Chronic Lymphocytic Leukemia," Journal of Leukocyte Biology 87(3):467-476, Society for Leukocyte Biology, United States (2010).
Dinarello, C.A., "Interleukin-1 in the Pathogenesis and Treatment of Inflammatory Diseases," Blood117(14):3720-3732, American Society of Hematology, United States (2011).
Du, R., et al., "HIF1 alpha Induces the Recruitment of Bone Marrow-derived Vascular Modulatory Cells to Regulate Tumor Angiogenesis and Invasion," Cancer Cell 13(3):206-220, Cell Press, United States (2008).
Eisenegger, C., et al., "The Role of Testosterone in Social Interaction," Trends in Cognitive Sciences 15(6):263-271, Elsevier Science, England (2011).
Engineer, D.R. and Garcia, J.M., "Leptin in Anorexia and Cachexia Syndrome," International Journal of Peptides 2012:Article ID 287457, Hindawi Publishing Corporation, United States (2012).
"Seoul National University Bundang Hospital excited because of '000'," Clinical trials of Dream Anticancer Drug without side effects with Kael & GemVax, 4 pages, Apr. 22, 2013.
Eustace, B.K. and Jay, D.G., "Extracellular Roles for the Molecular Chaperone, Hsp90," Cell Cycle 3(9):1098-1100, Taylor & Francis, United States (2004).
Eustace, B.K. and Jay, D.G., "Functional Proteomic Screens Reveal an Essential Extracellular Role for Hsp90 Alpha in Cancer Cell Invasiveness," Nature Cell Biology 6(6):507- 514, Macmillan Magazines Ltd., England (2004).
Evans, C.G., et al., "Heat Shock Protein 70 (Hsp70) as an Emerging Drug Target," Journal of Medicinal Chemistry 53(12):4585-4602, American Chemical Society, United States (2010).
Ferrarini, M., et al., "Unusual Expression and Localization of Heat-shock Proteins in Human Tumor Cells," International Journal of Cancer51(4):613-619, Wiley-Liss, United States (1992).
Fire, A., et al., "Potent and Specific Genetic Interference by Double-stranded RNA in Caenorhabditis Elegans," Nature 391(6669):806-811, Nature Publishing Group, England (1998).
Fittipaldi, A., et al., "Cell Membrane Lipid Rafts Mediate Caveolar Endocytosis of HIV-1 Tat Fusion Proteins," Journal of Biological Chemistry 278(36): 34141-34149, American Society for Biochemistry and Molecular Biology, United States (2003).
Fonseca, S.B., et al., "Recent Advances in the Use of Cell-Penetrating Peptides for Medical and Biological Applications," Advanced Drug Delivery Reviews 61(11):953-964, Elsevier Science Publishers, Netherlands (2009).
Fujii, H., et al., "Telomerase Insufficiency in Rheumatoid Arthritis," Proceedings of the National Academy of Sciences USA 106(11):4360-4365, National Academy of Sciences, United States (2009).
Garcia-Carbonero, R., et al., "Inhibition of HSP90 Molecular Chaperones: Moving Into the Clinic," The Lancet Oncology 14(9):e358-e369, Lancet Publishing Group, England (2013).
GemVax Receives Report on Anti-Inflammatory Mechanism, The Asia Economy Daily, Article written on May 7, 2013.
Ghaneh, P., et al., "Biology and Management of Pancreatic Cancer," Gut 56(8):1134-1152, British Medical Association, England (2007).
Gong, W., et al., "Invasion Potential of H22 Hepatocarcinoma Cells is Increased by HMGB1-induced Tumor NF-κB Signaling via Initiation of HSP70," Oncology Reports 30(3):1249-1256, D.A. Spandidos, Greece (2013).
Granger, D.N. and Korthuis, R.J., "Physiologic Mechanisms of Postischemic Tissue Injury," Annual Review of Physiology 57:311-332, Annual Reviews, United States (1995).
Gunturu, K.S., et al., "Immunotherapy Updates in Pancreatic Cancer: Are we there yet?," Therapeutic Advances in Medical Oncology 5(1):81-89, Sage, England (2013).
Guo, R.F., et al., "Regulatory Effects of Eotaxin on Acute Lung Inflammatory Injury," Journal of Immunology 166(8):5208-5218, American Association of Immunologists, United States (2001).
Heitz, F., et al., "Twenty Years of Cell-Penetrating Peptides: From Molecular Mechanisms to Therapeutics," British Journal of Pharmacology 157(2):195-206, Wiley, England (2009).
Heldin, C.H., et al., "TGF-Beta Signalling from Cell Membrane to Nucleus through SMAD Proteins," Nature 390(6659):465-471, Nature Publishing Group, England (1997).
Henry, J.Y., et al., "Lenalidomide Enhances the Anti-prostate Cancer Activity of Docetaxel in vitro and in vivo," The Prostate 72(8):856-867, Wiley-Liss, United States (2012).
Hse, "Rheumatoid arthritis," http://www.hse.ie/portal/eng, accessed at http://www.hse.ie/portal/eng/health/az/R/Rheumatoid-arthritis/, 14 pages (2013).
Inderberg-Suso, E.M., et al., "Widespread CD4+ T-cell Reactivity to Novel hTERT Epitopes following Vaccination of Cancer Patients with a Single hTERT Peptide GV1001," Oncoimmunology 1(5):670-686, Taylor and Francis, United States (2012).
International Preliminary Report on Patentability for Application No. PCT/KR2014/004752, The International Bureau of WIPO, Switzerland, dated Nov. 1, 2016, 23 pages.
International Preliminary Report on Patentability for Application No. PCT/KR2015/003642, The International Bureau of WIPO, Switzerland, dated Oct. 12, 2016, 18 pages.
International Preliminary Report on Patentability for International Application No. PCT/KR2014/011280, The International Bureau of WIPO, Geneva, Switzerland, dated May 24, 2016, 15 pages.
International Preliminary Report on Patentability for International Application No. PCT/EP2013/059460, International Bureau of WIPO, Switzerland, dated Nov. 11, 2014, 5 pages.
International Preliminary Report on Patentability for International Application No. PCT/KR2013/004145, The International Bureau of WIPO, Switzerland, dated Nov. 11, 2014,14 pages.
International Preliminary Report on Patentability for International Application No. PCT/KR2013/004176, The International Bureau of WIPO, Switzerland, dated Nov. 11, 2014,14pages.
International Preliminary Report on Patentability for International Application No. PCT/KR2013/006218, The International Bureau of WIPO, Switzerland, dated Jan. 13, 2015,27 pages.
International Preliminary Report on Patentability for International Application No. PCT/KR2013/008438, The International Bureau of WIPO, Switzerland, dated Mar. 24, 2015, 10 pages.
International Preliminary Report on Patentability for International Application No. PCT/KR2013/008445, The International Bureau of WIPO, Switzerland, dated Mar. 24, 2015, 13 pages.
International Preliminary Report on Patentability for International Application No. PCT/KR2014/003425, The International Bureau of WIPO, Switzerland, dated Oct. 20, 2015, 14 pages.
International Preliminary Report on Patentability for International Application No. PCT/KR2014/005031, The International Bureau of WIPO, Switzerland, dated Dec. 8, 2015, 8 pages.
International Preliminary Report on Patentability for International Application No. PCT/KR2014/005508, The International Bureau of WIPO, Switzerland, dated Jan. 5, 2016, 14 pages.
International Preliminary Report on Patentability for International Application No. PCT/KR2014/010035, Korean Intellectual Property Office, Republic of Korea, dated Apr. 26, 2016, 13 pages.

(56) References Cited

OTHER PUBLICATIONS

International Preliminary Report on Patentability for International Patent Application No. PCT/KR2013/004156, The International Bureau of WIPO, Geneva, Switzerland, dated Nov. 11, 2014, 15 pages.
International Search Report for International Application No. PCT/KR2014/003425, Korean Intellectual Property Office, Republic of Korea, dated Jul. 21, 2014, 8 pages.
International Search Report for International Application No. PCT/KR2014/011280, Korean Intellectual Property Office, Republic of Korea, dated Feb. 11, 2015, 12 pages.
International Search Report for International Application No. PCT/EP2013/059460, European Patent Office, Netherlands, dated Jul. 3, 2013, 5 pages.
International Search Report for International Application No. PCT/KR2013/004145, Korean Intellectual Property Office, Republic of Korea, dated Aug. 14, 2013, 10 pages.
International Search Report for International Application No. PCT/KR2013/004176, Korean Intellectual Property Office, Republic of Korea, dated Aug. 6, 2013, 10 pages.
International Search Report for International Application No. PCT/KR2013/006218, Korean Intellectual Property Office, Republic of Korea, dated Sep. 26, 2013, 8 pages.
International Search Report for International Application No. PCT/KR2013/008438, Korean Intellectual Property Office, Republic of Korea, dated Dec. 23, 2013, 8 pages.
International Search Report for International Application No. PCT/KR2013/008445, Korean Intellectual Property Office, Republic of Korea, dated Dec. 23, 2013, 10 pages.
International Search Report for International Application No. PCT/KR2014/004752, Korean Intellectual Property Office, Republic of Korea, dated Jan. 16, 2015, 10 pages.
International Search Report for International Application No. PCT/KR2014/005031, Korean Intellectual Property Office, Republic of Korea, dated Sep. 22, 2014, 6 pages.
International Search Report for International Application No. PCT/KR2014/005508, Korean Intellectual Property Office, Republic of Korea, dated Oct. 14, 2014, 8 pages.
International Search Report for International Application No. PCT/KR2014/010035, Korean Intellectual Property Office, Republic of Korea, dated Feb. 2, 2015, 8 pages.
International Search Report for International Application No. PCT/KR2015/003642, Korean Intellectual Property Office, Republic of Korea, dated Jul. 3, 2015, 8 pages.
International Search Report for International Patent Application No. PCT/KR2013/004156, Korean Intellectual Property Office, Republic of Korea, dated Aug. 14, 2013, 10 pages.
International Search Report for International Application No. PCT/KR2014/012502, Korean Intellectual Property Office, Republic of Korea, dated Mar. 11, 2015, 10 pages.
International Search Report for International Application No. PCT/KR2013/008459, Korean Intellectual Property Office, Republic of Korea, dated Dec. 23, 2013, 8 pages.
International Preliminary Report on Patentability for International Application No. PCT/KR2014/012502, The International Bureau of WIPO, Geneva, Switzerland, dated Jun. 21, 2016, 22 pages.
Jaattela, M., "Over-expression of Hsp70 Confers Tumorigenicity to Mouse Fibrosarcoma Cells," International Journal of Cancer 60(5):689-693, Wiley-Liss, United States (1995).
Jemal, A., et al., "Cancer Statistics, 2008," CA: A Cancer Journal for Clinicians 58(2):71-96, Wiley, United States (2008).
Kern, K.A. and Norton, J.A., "Cancer Cachexia," Journal of Parenteral and Enteral Nutrition 12(3):286-298, Sage Publications, United States (1988).
Kim, B.K., et al., "Tumor-suppressive Effect of a Telomerase-derived Peptide by Inhibiting Hypoxia-induced HIF-1α-VEGF Signaling Axis," Biomaterials 35(9):2924-2933, Elsevier Science, Netherlands (2014).
Kim, H.O. and Lee, S.I., "Experimental Animal Models for Rheumatoid Arthritis: Methods and Applications," Journal of Rheumatic Diseases 19(4):189-195, The Korean College of Rheumatology, Republic of Korea(2012).
Kocsis, J., et al., "Serum Level of Soluble 70-kD Heat Shock Protein Is Associated With High Mortality in Patients With Colorectal Cancer Without Distant Metastasis," Cell Stress & Chaperones 15(2):143-151, Springer, Netherlands (2010).
Kokhaei, P., et al., "Telomerase (hTERT 611-626) Serves as a Tumor Antigen in B-cell Chronic Lymphocytic Leukemia and Generates Spontaneously Antileukemic, Cytotoxic T Cells," Experimental Hematology 35(2):297-304, Elsevier Science Inc., Netherlands (2007).
Kyte, J.A., "Cancer Vaccination with Telomerase Peptide GV1001," Expert Opinion on Investigational Drugs 18(5):687-694, Taylor & Francis, England (2009).
Lahdevirta, J., et al., "Elevated Levels of Circulating Cachectin/tumor Necrosis Factor in Patients with Acquired Immunodeficiency Syndrome," American Journal of Medicine 85(3):289-291, Excerpta Medica, United States (1988).
Laviano, A., et al., "Therapy Insight: Cancer Anorexia-cachexia Syndrome—When All You Can Eat is Yourself," Nature Clinical Practice. Oncology 2(3):158-165, Nature Publishing Group, England (2005).
Lee, S.A., et al., "Heat Shock Protein-Mediated Cell Penetration and Cytosolic Delivery of Macromolecules by a Telomerase-Derived Peptide Vaccine," Biomaterials 34(30):7495-7505, Elsevier Science, Netherlands (2013).
Liu, Q.J., et al., "Rapamycin Enhances the Susceptibility of Both Androgen-dependent and -independent Prostate Carcinoma Cells to Docetaxel," Chinese Medical Journal 123(3):356-360, Chinese Medical Association, China (2010).
Luft, R., et al., "A Case of Severe Hypermetabolism of Nonthyroid Origin with a Defect in the Maintenance of Mitochondrial Respiratory Control: A Correlated Clinical, Biochemical, and Morphological Study," Journal of Clinical Investigation 41:1776-1804, American Society for Clinical Investigation, United States (1962).
Martinez, P. and Blasco, M.A., "Telomeric and Extra-telomeric Roles for Telomerase and the Telomere-binding Proteins," Nature Reviews Cancer 11(3):161-176, Nature Publishing Group, England (2011).
Massague, J., "Tgf-Beta Signal Transduction," Annual Review of Biochemistry 67:753-791, Annual Reviews, United States (1998).
Mattson, M.P., "Pathways Towards and Away From Alzheimer's Disease," Nature 430(7000):631-639, Nature Publishing Group, England (2004).
McConnell, J.D., et al., "The Effect of Finasteride on the Risk of Acute Urinary Retention and the Need for Surgical Treatment Among Men with Benign Prostatic Hyperplasia. Finasteride Long-term Efficacy and Safety Study Group," The New England Journal of Medicine 338(9):557-563, Massachusetts Medical Society, United States (1998).
Modica-Napolitano, J.S. and Singh, K.K., "Mitochondria as Targets for Detection and Treatment of Cancer," Expert Reviews in Molecular Medicine 4(9):1-19, Cambridge University Press, England (2002).
Morano, K.A., "New Tricks for an Old Dog: the Evolving World of Hsp70," Annals of the New York Academy of Sciences 1113:1-14, Blackwell, United States (2007).
Morishita, M., and Peppas, N.A., "Is the Oral Route Possible for Peptide and Protein Drug Delivery?," Drug Discovery Today 11(19-20):905-910, Elsevier Science Ltd., England (2006).
Murphy, M.E., "The Hsp70 Family and Cancer," Carcinogenesis 34(6):1181-1188, Irl Press, England (2013).
Myers, L.K., et al., "Collagen-Induced Arthritis, an Animal Model of Autoimmunity," Life Sciences 61(19):1861-1878, Elsevier, Netherlands (1997).
Nagaraju, G.P., et al., "Antiangiogenic Effects of Ganetespib in Colorectal Cancer Mediated Through Inhibition of HIF-1α and STAT-3," Angiogenesis 16(4):903-917, Springer, Germany (2013).
National Horizon Scanning Centre News on Emerging Technologies in Healthcare, GV1001 for Advanced and/or Metastatic Pancreatic Cancer, Published Apr. 2008.

(56) References Cited

OTHER PUBLICATIONS

National Institute of Diabetes and Digestive and Kidney Diseases, "Prostate Enlargement: Benign Prostatic Hyperplasia," Updated Sep. 2014, 14 pages.
NCBI, Reference Sequence: XP_003776612.1 (Jul. 17, 2012).
Novina, C.D. and Sharp, P.A., "The RNAi Revolution," Nature 430(6996):161-164, Nature Publishing Group, England (2004).
Oh, H., et al., "Telomerase Reverse Transcriptase Promotes Cardiac Muscle Cell Proliferation, Hypertrophy, and Survival," Proceedings of the National Academy of Sciences USA 98(18): 10308-10313, National Academy of Sciences, United States (2001).
Pearson, W.R. and Lipman, D.J., "Improved Tools for Biological Sequence Comparison," Proceedings of the National Academy of Sciences USA 85(8):2444-2448, National Academy of Sciences, United States (1988).
Perez, R.G., et al., "The Beta-amyloid Precursor Protein of Alzheimer's Disease Enhances Neuron Viability and Modulates Neuronal Polarity," The Journal of Neuroscience 17(24):9407- 9414, Society for Neuroscience, United States (1997).
Pfosser, A., et al., "Liposomal HSP90 Cdna Induces Neovascularization via Nitric Oxide in Chronic Ischemia," Cardiovascular Research 65(3):728-736, Oxford Journals, England (2005).
Powers, M.V., et al., "Targeting HSP70: the Second Potentially Druggable Heat Shock Protein and Molecular Chaperone?," Cell Cycle 9(8):1542-1550, Taylor & Francis, United States (2010).
Rana, T.M., "Illuminating the Silence: Understanding the Structure and Function of Small RNAs," Nature Reviews. Molecular Cell Biology 8(1):23-36, Nature Publishing Group, England (2007).
Rheumatoid Arthritis from Merck Manual, accessed on Apr. 21, 2016, pp. 1-18.
Roubenoff, R., et al., "Adjuvant Arthritis as a Model of Inflammatory Cachexia," Arthritis and Rheumatism 40(3):534-539, Wiley-Blackwell, United States (1997).
Sayers, S., et al., "Vaxjo: A Web-based Vaccine Adjuvant Database and its Application for Analysis of Vaccine Adjuvants and their Uses in Vaccine Development," Journal of Biomedicine and Biotechnology 2012:1-13, Article ID 831486, Hindawi Publishing Corporation, United States (2012).
Schenk, D., et al., "Immunization with Amyloid-beta Attenuates Alzheimer-disease-like Pathology in the PDAPP Mouse," Nature 400(6740):173-177, Nature Publishing Group, England (1999).
Schlapbach, C., et al., "Telomerase-specific GV1001 Peptide Vaccination Fails to Induce Objective Tumor Response in Patients with Cutaneous T Cell Lymphoma," Journal of Dermatological Science 62(2):75-83, Elsevier, Netherlands (2011).
Seo, J.S., et al., "T Cell Lymphoma in Transgenic Mice Expressing the Human Hsp70 Gene," Biochemical and Biophysical Research Communications 218(2):582-587, Elsevier, United States (1996).
Shaw, V.E., et al., "Current Status of GV1001 and Other Telomerase Vaccination Strategies in the Treatment of Cancer," Expert Review of Vaccines 9(9):1007-1016, Taylor & Francis, England (2010).
Shay, J.W., and Wright, W.E., "Telomerase Therapeutics for Cancer: Challenges and New Directions," Nature Reviews. Drug Discovery 5(7):577-584, Nature Publishing Group, England (2006).
Smith, D.B. and Johnson, K.S., "Single-step Purification of Polypeptides Expressed in *Escherichia coli* as Fusions with Glutathione 5-transferase," Gene 67(1):31-40, Elsevier, Netherlands (1988).
Smith, T.F. and Waterman, M.S., "Comparison of Biosequences," Advances in Applied Mathematics 2(4):482-489, Academic Press, Inc., United States (1981).
Song, J., et al., "Characterization and Fate of Telomerase-Expressing Epithelia during Kidney Repair," Journal of the American Society of Nephrology 22(12):2256-2265, American Society of Nephrology, United States (2011).
Southern Cross, "Rheumatoid arthritis—causes, symptoms, and treatment," https://www.southerncross.co.nz/, accessed at https://www.southerncross.co.nz/AboutTheGroup/HealthResources/MedicalLibrary/tabid/178/vw/1/itemID/124/Rheumatoid-arthritis-causes-symptoms-treatment.aspx, last reviewed on May 31, 2013, 5 pages.

Stevenson, C.L., "Advances in Peptide Pharmaceuticals," Current Pharmaceutical Biotechnology 10(1):122-137, Bentham Science Publishers, United Arab Emirates (2009).
Sun, J., et al., "Induction of Angiogenesis by Heat Shock Protein 90 Mediated by Protein Kinase Akt and Endothelial Nitric Oxide Synthase," Arteriosclerosis, Thrombosis, and Vascular biology 24(12):2238-2244, Lippincott Williams & Wilkins, United States (2004).
Taylor, P.C. and Feldmann, M., "Anti-TNF Biologic Agents: Still the Therapy of Choice for Rheumatoid Arthritis," Nature Reviews. Rheumatology 5(10):578-582, Macmillan Publishers Limited, England (2009).
Sasada, A., et al., "A Case of Elderly Patient With Lung Cancer Efficiently Treated With Dendritic Cell Immunotherapy," the 20th International Congress of Personalized Medicine, Conference Program and Abstracts, Personalized Medicine Universe (Japanese edition) 4(Supplement 1): 2 pages, May 24, 2015.
Kawasaki, H., et al., "Detection and Evaluation of Activation of Various Cancer Antigenic Peptide-specific CTLs in Mature Dendritic Cells Used for Dendritic Cell Therapy," The21st International Congress of Personalized Medicine, Conference Program and Abstracts, Personalized Medicine Universe (Japanese edition) 4(Supplement 2): 2 pages, Oct. 17, 2015.
Thompson, J.D., et al., "CLUSTAL W: Improving the Sensitivity of Progressive Multiple Sequence Alignment Through Sequence Weighting, Position-specific Gap Penalties and Weight Matrix Choice," Nucleic Acids Research 22(22):4673-4680, Oxford University Press, England (1994).
Tisdale, M.J., "Mechanisms of Cancer Cachexia," Physiological Reviews 89(2):381-410, American Physiological Society, United States (2009).
Tomari Y. and Zamore, P.D., "Perspective: Machines for RNAi," Genes and Development 19(5):517-529, Cold Spring Harbor Laboratory Press, United States (2005).
Uehara, Y., "Natural Product Origins of Hsp90 Inhibitors," Current Cancer Drug Targets 3(5):325-330, Bentham Science Publishers, Netherlands (2003).
Van Coppenolle, F., et al., "Effects of Hyperprolactinemia on Rat Prostate Growth: Evidence of Androgeno-dependence," American Journal of Physiology. Endocrinology and Metabolism 280(1):E120-E129, American Physiological Society, United States (2001).
Vanbuskirk, A., et al., "A Peptide Binding Protein Having a Role in Antigen Presentation Is a Member of the HSP70 Heat Shock Family," The Journal of Experimental Medicine 170(6):1799-1809, Rockefeller University Press, United States (1989).
Vennela, B., et al., "Current and Future Strategies for Therapy of Pancreatic Cancer," International Journal of Research in Pharmacy and Medicine 2(3):728-740 (2012).
Volloch, V.Z. and Sherman, M.Y., "Oncogenic Potential of Hsp72," Oncogene 18(24):3648-3651, Nature Publishing Group, England (1999).
Walsmith, J. and Roubenoff, R., "Cachexia in Rheumatoid Arthritis," International Journal of Cardiology 85(1):89-99, Elsevier, Netherlands (2002).
Wang, W., et al., "Alleviating the Ischemia-Reperfusion Injury of Donor Liver by Transfection of Exogenous hTERT Genes," Transplantation Proceedings 41(5):1499-1503, Elsevier Science, United States (2009).
Written Opinion for International Application No. PCT/KR2014/011280, Korean Intellectual Property Office, Republic of Korea, dated Feb. 11, 2015, 14 pages.
Written Opinion for International Application No. PCT/EP2013/059460, European Patent Office, Germany, dated Jul. 3, 2013, 4 pages.
Written Opinion for International Application No. PCT/KR2013/004145, Korean Intellectual Property Office, Republic of Korea, dated Aug. 14, 2013, 13 pages.
Written Opinion for International Application No. PCT/KR2013/004176, Korean Intellectual Property Office, Republic of Korea, dated Aug. 6, 2013, 13 pages.
Written Opinion for International Application No. PCT/KR2013/006218, Korean Intellectual Property Office, Republic of Korea, dated Sep. 26, 2013, 26 pages.

(56) References Cited

OTHER PUBLICATIONS

Written Opinion for International Application No. PCT/KR2013/008438, Korean Intellectual Property Office, Republic of Korea, dated Dec. 23, 2013, 9 pages.
Written Opinion for International Application No. PCT/KR2013/008445, Korean Intellectual Property Office, Republic of Korea, dated Dec. 23, 2013, 12 pages.
Written Opinion for International Application No. PCT/KR2014/004752, Korean Intellectual Property Office, Republic of Korea, dated Jan. 16, 2015, 21 pages.
Written Opinion for International Application No. PCT/KR2014/005031, Korean Intellectual Property Office, Republic of Korea, dated Sep. 22, 2014, 7 pages.
Written Opinion for International Application No. PCT/KR2014/005508, Korean Intellectual Property Office, Republic of Korea, dated Oct. 14, 2014, 13 pages.
Written Opinion for International Application No. PCT/KR2014/010035, Korean Intellectual Property Office, Republic of Korea, dated Feb. 2, 2015, 11 pages.
Written Opinion for International Application No. PCT/KR2015/003642, Korean Intellectual Property Office, Republic of Korea, dated Jul. 3, 2015, 16 pages.
Written Opinion for International Application No. PCT/KR2013/008459, Korean Intellectual Property Office, Republic of Korea, dated Dec. 23, 2013, 9 pages.
Written Opinion for International Patent Application No. PCT/KR2013/004156, Korean Intellectual Property Office, Republic of Korea, dated Aug. 14, 2013, 13 pages.
Written Opinion for International Application No. PCT/KR2014/003425, Korean Intellectual Property Office, Republic of Korea, dated Jul. 21, 2014, 13 pages.
Written Opinion for International Application No. PCT/KR2014/012502, Korean Intellectual Property Office, Republic of Korea, dated Mar. 11, 2015, 20 pages.
Yankner, B.A., et al., "Neurotrophic and Neurotoxic Effects of Amyloid Beta Protein: Reversal by Tachykinin Neuropeptides," Science 250(4978):279-282, American Association for the Advancement of Science, United States (1990).
Yeh, C.H., et al., "Clinical Correlation of Circulating Heat Shock Protein 70 in Acute Leukemia," Leukemia Research 34(5):605-609, Pergamon Press, England (2010).
Yi, a., et al., "Radiation-Induced Complications after Breast Cancer Radiation Therapy: a Pictorial Review of Multimodality Imaging Findings," Korean Journal of Radiology 10(5):496-507, Korean Society of Radiology, Korea (2009).
Zhang, H., et al., "Inhibiting TGFβ1 has a Protective Effect on Mouse Bone Marrow Suppression Following Ionizing Radiation Exposure in Vitro," Journal of Radiation Research 54(4):630-636, Oxford University Press, England (2013).
Zhou, J., et al., "PI3K/Akt Is Required for Heat Shock Proteins to Protect Hypoxia-inducible Factor 1 alpha From pVHL-independent Degradation," The Journal of Biological Chemistry 279(14):13596-13513, American Society for Biochemistry and Molecular Biology, United States (2004).
ClinicalTrials.gov, "Adjuvant Leuprolide with or without Docetaxel in High Risk Prostate Cancer After Radial Prostatectomy," Identifier NCT00283062, first received on Jan. 26, 2006, accessed at https://clinicaltrials.gov/ct2/show/study/NCT00283062, last accessed on May 12, 2017, 7 pages.
ClinicalTrials.gov, "Gemcitabine, Capecitabine, and Telomerase Peptide Vaccine GV1001 in Treating Patients With Locally Advanced and Metastatic Pancreatic Cancer," Identifier NCT00425360, accessed at https://clinicaltrials.gov/archive/NCT00425360/2007_01_22, last accessed on Apr. 7, 2017, 4 pages.
Allergic Rhinitis from Merck Manual, pp. 1-4. Accessed Nov. 2, 2017.
Asthma from Merck Manual, pp. 1-4. Accessed Nov. 2, 2017.

De Araujo, J.G., et al., "The Potential Use of Melatonin for Preventing Cisplatin Ototoxicity: An Insight for a Clinical Approach," Advances in Otolaryngology 2014:8 pages, Hindawi Publishing Corporation (2014).
International Preliminary Report on Patentability and Written Opinion for International Application No. PCT/KR2015/014099, The International Bureau of WIPO, dated Jun. 27, 2017, 16 pages.
International Search Report for International Application No. PCT/KR2015/014099, Korean Intellectual Property Office, Republic of Korea, dated May 4, 2016, 8 pages.
International Search Report for International Application No. PCT/KR2016/001646, Korean Intellectual Property Office, Republic of Korea, dated May 20, 2016, 8 pages.
Kim, B.H., "Presbycusis: Review for its Environmental Risk Factors," Korean Journal of Otorhinolaryngology—Head and Neck Surgery 49(10):962-967, Korean Society of Otolaryngology—Head and Neck Surgery, Korea (2006).
Kyte, J.A., et al., "Telomerase Peptide Vaccination Combined with Temozolomide: A Clinical Trial in Stage IV Melanoma Patients," Clinical Cancer Research 17(13):4568-4580, American Association of Cancer Research, United States (2011).
Lee, E.K., et al., "Inhibition of Experimental Choroidal Neovascularization by Telomerase-derived Peptide GV1001," Investigative Ophthalmology & Visual Science 56(7):Abstract 2291, ARVO Annual Meeting Abstract (Jun. 2015).
Mandal, A., "Types of Fibrosis," Retrieved from the internet on Jul. 3, 2014, pp. 1-3.
Middleton, G., et al., "Gemcitabine and Capecitabine With or Without Telomerase Peptide Vaccine GV1001 in Patients With Locally Advanced or Metastatic Pancreatic Cancer (TeloVac): an Open-label, Randomised, Phase 3 Trial," The Lancet. Oncology 15(8):829-840, Lancet Pub. Group, England (2014).
National Center for Biotechnology Information, "Hormones," MeSH Database, Bethesda, accessed at http://www.ncbi.nlm.nih.gov/mesh/68006728, accessed on May 8, 2017, 3 pages.
Nawroth, I., et al., "Intraperitoneal Administration of Chitosan/DsiRNA Nanoparticles Targeting TNFα Prevents Radiation-induced Fibrosis," Radiotherapy and Oncology 97(1):143-148, Elsevier Scientific Publishers, Ireland (2010).
Rosenbloom, J., et al., "Strategies for Anti-fibrotic Therapies," Biochimica et Biophysica Acta 1832(7):1088-1103, Elsevier Pub. Co., Netherlands (2013).
Rowe-Rendleman, C. and Glickman, R.D., "Possible therapy for age-related macular degeneration using human telomerase," Brain Research Bulletin 62(6):549-553, Elsevier Science Inc., United States (2004).
Tisdale, M.J., "Catabolic Mediators of Cancer Cachexia," Current Opinion in Supportive and Palliative Care, 2(4):256-261, Lippincott Williams & Wilkins, United States (2008).
Wynn, T.A. and Ramalingam, T.R., "Mechanisms of Fibrosis: Therapeutic Translation for Fibrotic Disease," Nature Medicine 18(7):1028-1040, Nature Publishing Company, United States (2012).
Cystic Fibrosis from Merck Manual, pp. 1-15, Accessed Nov. 2, 2017.
Albini, A., et al., "Cancer Prevention by Targeting Angiogenesis," Nature reviews Clinical oncology 9(9):498-509, Nature Pub Group (2012).
Auerbach, R., et al., "Angiogenesis Assays: Problems and Pitfalls," Cancer Metastasis Reviews 19(1-2):167-172, Kluwer Academic, Netherlands (2000).
Berendsen, H.J., "A Glimpse of the Holy Grail?," Science 282(5389):642-643, American Association for the Advancement of Science, United States (1998).
Du, C., et al., "Conformational and Topological Requirements of Cell-permeable Peptide Function," The Journal of Peptide Research 51(3):235-243, Munksgaard, Denmark (1998).
Extended European Search Report for Application No. EP14808179, dated May 24, 2017, 24 pages.
Fauce, S.R., et al., "Telomerase-Based Pharmacologic Enhancement of Antiviral function of Human CD8+ T Lymphocytes," Immunology 181(10):7400-7406, American Association of Immunologists, United States (Nov. 2008).

(56) References Cited

OTHER PUBLICATIONS

Fontanes, V., et al., "A cell permeable peptide inhibits Hepatitis C Virus Replication by Sequestering IRES Transacting Factors," Virology 394(1):82-90, Academic Press, United States (Nov. 2009).
International Preliminary Report on Patentability and Written Opinion for International Application No. PCT/KR2016/001646, Korean Intellectual Property Office, Republic of Korea, dated May 20, 2016, 13 pages.
International Search Report for Application No. PCT/KR2016/007192, dated Sep. 12, 2016, 12 pages.
Jain, R.K., "Barriers to Drug Delivery in Solid Tumors," Scientific American 271(1):58-65, Scientific American, Inc., United States (Jul. 1994).
Kalnins, A., et al., "Sequence of the Lacz Gene of Escherichia coli," The EMBO Journal 2(4):593-597, Wiley Blackwell, England (1983).
Kim, H., et al., "Inhibition of HIV-1 Reactivation by a Telomerase-Derived Peptide in a HSP90-Dependent Manner," Scientific Reports 6: 28896, Nature Publishing Group, England (Jul. 2016).
Lee, S.A., et al., "A Telomerase-Derived Peptide Regulates Reactive Oxygen Species and Hepatitis C Virus RNA Replication in HCV-Infected Cells via Heat Shock Protein 90, "Biochemical and Biophysical Research Communications 471(1):156-162, Elsevier, United States (Feb. 2016).
Leem G., et al., Immunotherapy in Pancreatic Cancer; the Road Less Traveled Immunol Disord Immunotherapy, Jun. 26, 2016 (Jun. 26, 2016), p. 1000106, XP055328627, Retrieved from the Internet: (URL:http://www.omicsgroup.orgjjournalsjimmunotherapy-in-pancreatic-cancer-the-road-less-traveled-IDIT-1000104.pdf), six pages.
Merck, "Obesity, The Merck Manual Professional Edition," accessed at https://www.merckmanuals.com/professional/nutritional-disorders/obesity-and-the-metabolic-syndrome/obesity, accessed on Oct. 6, 2014, 9 pages.
Middleton, G.W., "A Phase III Randomized Trial of Chemoimmunotherapy Comprising Gemcitabine and Capecitabine with or Without Telomerase Vaccine GV1001 in Patients with Locally Advanced or Metastatic Pancreatic Cancer," Presented at conference ASCO, (Jun. 4, 2013), XP054977010. Retrieved from the Internet: (URL: http://meetinglibrary.asco.orgjcontent/82894?media=vm).
Middleton, G.W., et al., Phase III Randomized Trial of Chemoimmunotherapy Comprising Gemcitabine and Capecitabine with or without Telomerase Vaccine GV1001 in Patients with Locally Advanced or Metastatic Pancreatic Cancer, ASCO Annual Meeting, 31:1-3, (May 31, 2013)-(Jun. 4, 2013), XP055328310.
Middleton, G.W., et al., Poster: Predictive Cytokine Biomarkers for Survival in Patients with Advanced Pancreatic Cancer Randomized to Sequential Chemoimmunotherapy Comprising Gemcitabine and Capecitabine (GemCap) Followed by the Telomerase Vaccine GV1001 Compared to Concurrent Chemoimmunotherapy in the Telovac Phase III tr, ASCO 2014, May 30, 2014 (May 30, 2014)-Jun. 3, 2014 (Jun. 3, 2014), pp. 1-1. XP055328448. Retrieved from the Internet: (URL:http://media4.asco.org/144/8599/93976/93976_poster_pvhr.jpg).
Neoptolemos J.P., et al., "Predictive 1-20 Cytokine Biomarkers for Survival in Patients With Advanced Pancreatic Cancer Randomized to Sequential Chemoimmunotherapy Comprising Gemcitabine and Capecitabine (Gemcap) Followed by the Telomerase Vaccine GV1001 Compared to Concurrent Chemoimmunotherapy in the Telovac Phase III trial," 2014 ASCO Annual Meeting, May 30, 2014 (May 30, 2014)-Jun. 3, 2014 (Jun. 3, 2014), pp. 1-3.
Ngo. et al., "Computational Complexity, Protein Structure Prediction, and the Levinthal Paradox," in The Protein Folding Problem and Tertiary Structure Prediction, Merz, Jr., K.M., and Le Grand, S.M., eds., pp. 491-494, Birkhauser Boston, United States (1994).
O'Beirne, J., et al., "Generation of Functional CD8+ T Cells by Human Dendritic Cells Expressing Glypican-3 Epitopes," in: Journal of Experimental and Clinical Cancer Research 29:48, pp. 1-11, BioMed Central, London (May 2010).
Priya, S.G., et al., "Skin Tissue Engineering for Tissue Repair and Regeneration," Tissue Engineering. Part B, Reviews 14(1):105-118, Mary Ann Liebert, Inc., United States (2008).
Rudinger, J., "Characteristics of the Amino Acids as Components of a Peptide Hormone Sequence," in Peptide Hormones, Parsons, J.A., ed., University Park Press, United States (1976).
Schwarze, S.R., et al., "In Vivo Protein Transduction: Delivery of a Biologically Active Protein Into the Mouse," Science 285(5433):1569-1572, American Association for the Advancement of Science, United States (1999).
Sigma Genosys, "Designing Custom Peptides," accessed at http://www.sigma-genosys.com/peptide_design.asp, Accessed on Dec. 16, 2004, 2 pages.
Supplemental European Search Report for Application No. EP14808179, dated Jan. 10, 2017, 13 pages.
Varma, N., et al., "Role of hTERT and WT1 Gene Expression in Disease Progression and Imatinib Responsiveness of Patients with BCR-ABL Positive Chronic Myeloid Leukemia," in: Leukemia and Lymphoma 52(4):687-693, Informa Healthcare, London (Apr. 2011).
Voet, D. and Voet, J.G., "Abnormal Hemoglobins," in Biochemistry, 2nd Edition, Chapter 9, pp. 235-241, John Wiley & Sons, Inc., United States (1995).
Westin, E.R., et al., "The p53/p21(WAF/CIP) Pathway Mediates Oxidative Stress and Senescence in Dyskeratosis Congenita Cells With Telomerase Insufficiency," Antioxidants & Redox Signaling 14(6):985-997, Mary Ann Liebert, Inc., United States (2011).
Written opinion for Application No. PCT/KR2016/007192, dated Sep. 12, 2016, 16 pages.
International Search Report and Written Opinion for International Application No. PCT/KR2016/012613, Korean Intellectual Property Office, Republic of Korea, dated Feb. 2, 2017, 14 pages.
Kirino, T, "Delayed Neuronal Death in the Gerbil Hippocampus Following Ischemia," Brain Research 239(1):57-69, Amsterdam Elsevier/North-Holland Biomedical Press, Netherlands (May 1982).
Olney, J.W., et al., "Pathological Changes Induced in Cerebrocortical Neurons by Phencyclidine and Related Drugs," Science 244(4910):1360-1362, American Association for the Advancement of Science, United States (Jun. 1989).
Hochreiter, W.W., "Anti-Inflammatory Therapies for Chronic Prostatitis," European Urology Supplements 2:30-33, Elsevier, Netherlands (2003).
Pontari, M.A., et al., "Inflammation and Anti-inflammatory therapy in Chronic Prostatitis," Urology 60:6A: 29-33, Elsevier, Netherlands (2002).
Godet, Y., et al. "Analysis of spontaneous tumor-specific CD4 T-cell immunity in lung cancer using promiscuous HLA-DR telomerase-derived epitopes: potential synergistic effect with chemotherapy response." Clinical Cancer Research 18(10): 2943-2953, American Association for Cancer Research (2012).

* cited by examiner

FIG.3
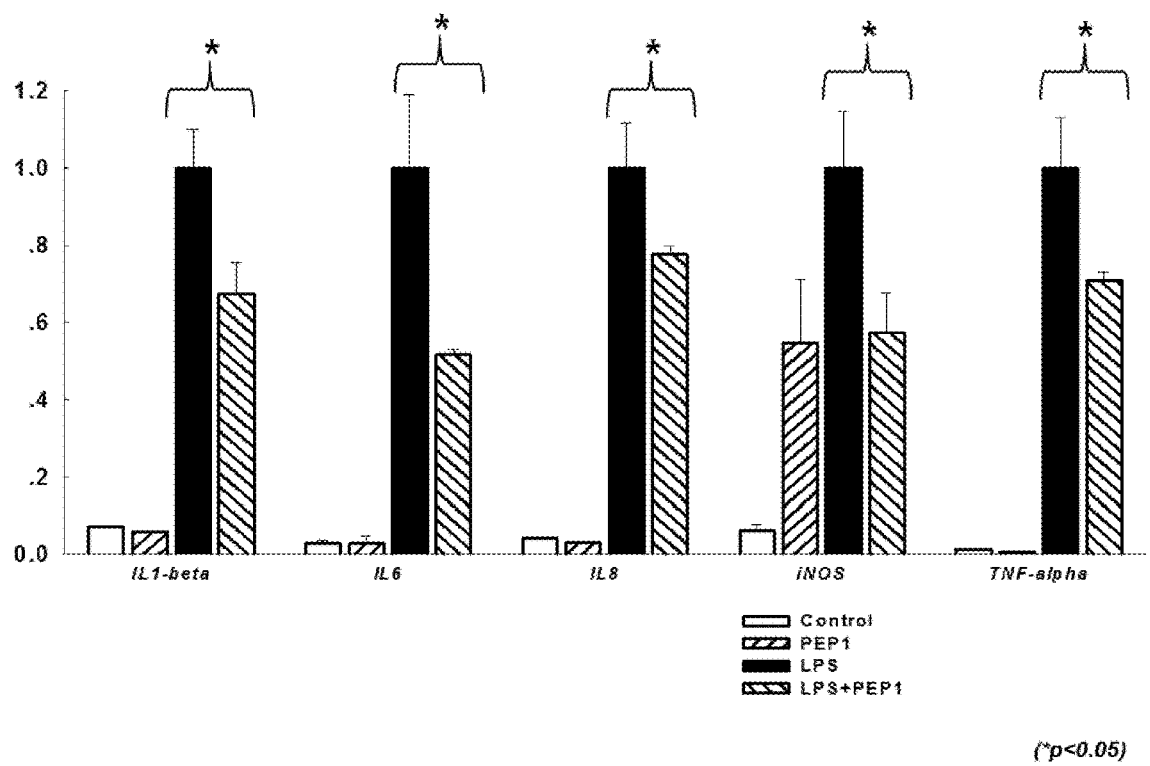
(*p<0.05)
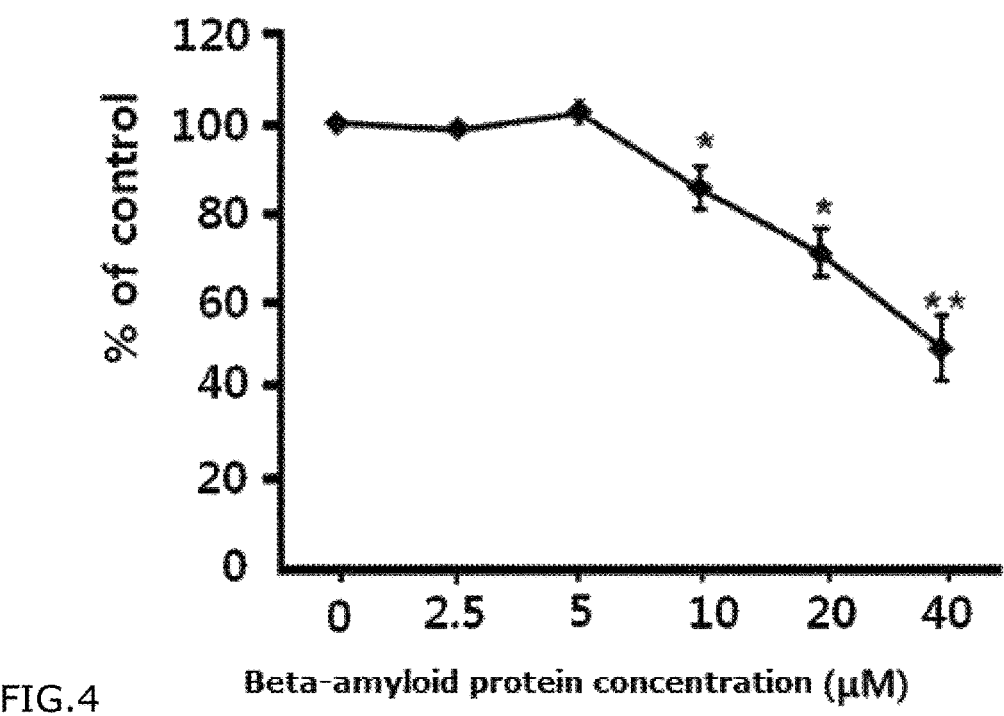
FIG.4

FIG.5
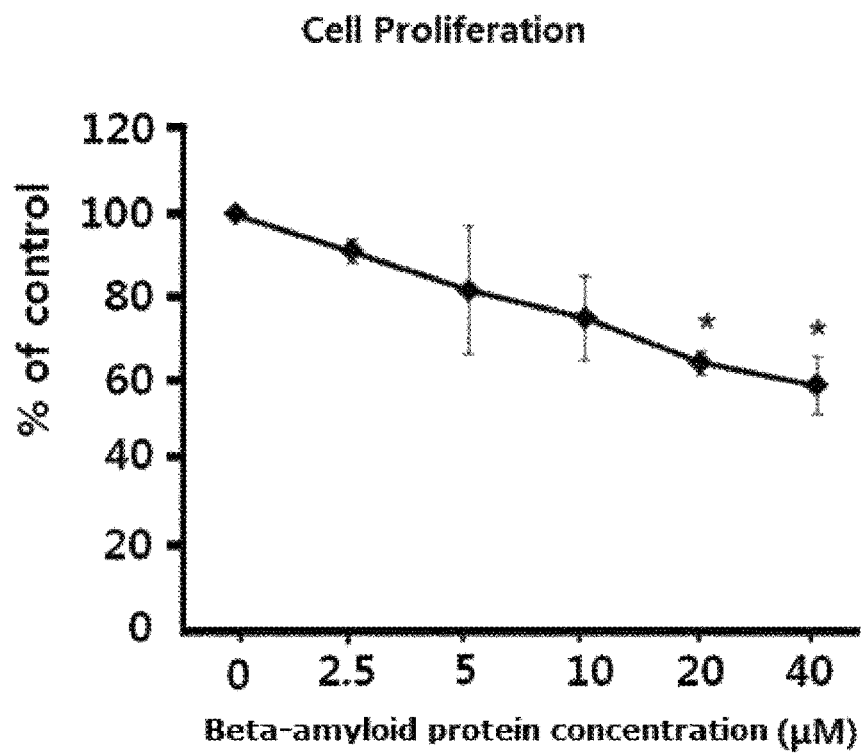
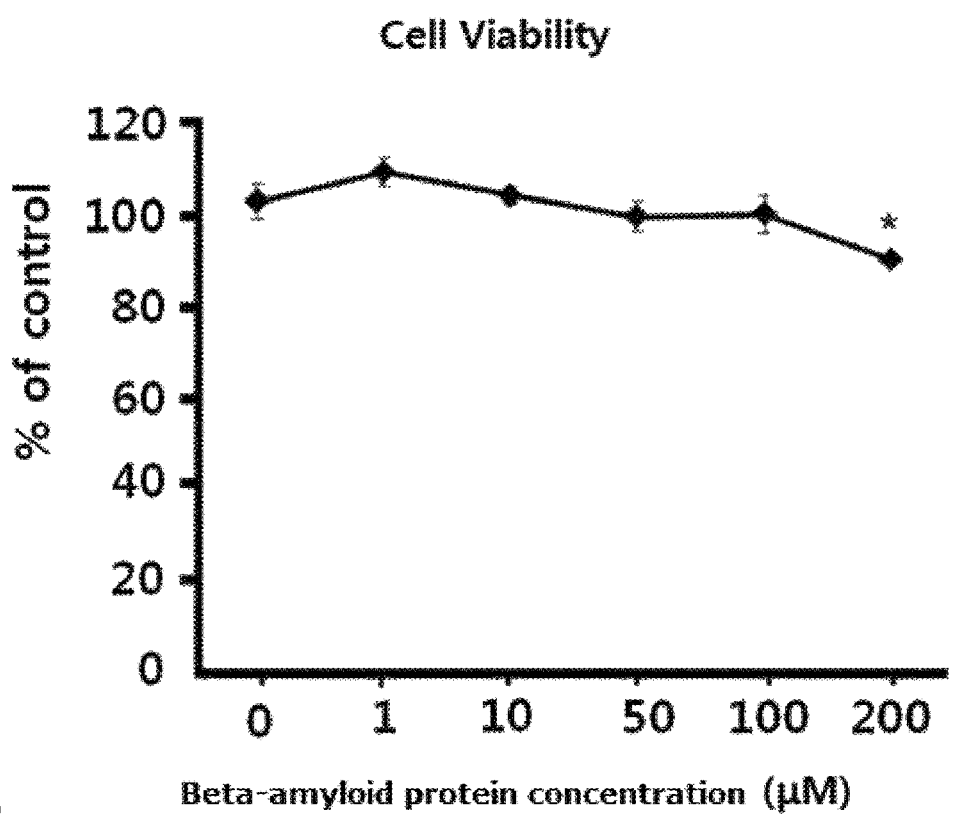
FIG.6

SEQUENCE LISTING

<160> NUMBER OF SEQ ID NOS: 13

<210> SEQ ID NO 1
<211> LENGTH: 16
<212> TYPE: PRT
<213> ORGANISM: Homo sapiens

<400> SEQUENCE: 1

Glu Ala Arg Pro Ala Leu Leu Thr Ser Arg Leu Arg Phe Ile Pro Lys
1               5                   10                  15

<210> SEQ ID NO 2
<211> LENGTH: 20
<212> TYPE: DNA
<213> ORGANISM: Artificial Sequence
<220> FEATURE:

<223> OTHER INFORMATION: forward primer for TNF-alpha

<400> SEQUENCE: 2
ctatctggga ggggtcttcc                                        20

<210> SEQ ID NO 3
<211> LENGTH: 20
<212> TYPE: DNA
<213> ORGANISM: Artificial Sequence
<220> FEATURE:
<223> OTHER INFORMATION: reverse primer for TNF-alpha

<400> SEQUENCE: 3
atgttcgtcc tgctcacagg                                        20

<210> SEQ ID NO 4
<211> LENGTH: 20
<212> TYPE: DNA
<213> ORGANISM: Artificial Sequence
<220> FEATURE:
<223> OTHER INFORMATION: forward primer for il-1 beta

<400> SEQUENCE: 4
ggacaagctg aggaagatgc                                        20

<210> SEQ ID NO 5
<211> LENGTH: 20
<212> TYPE: DNA
<213> ORGANISM: Artificial Sequence
<220> FEATURE:
<223> OTHER INFORMATION: reverse primer for il-1 beta

<400> SEQUENCE: 5
tcgttatccc atgagtcgaa                                        20

<210> SEQ ID NO 6
<211> LENGTH: 22
<212> TYPE: DNA
<213> ORGANISM: Artificial Sequence
<220> FEATURE:
<223> OTHER INFORMATION: forward primer for il-6

<400> SEQUENCE: 6
aaaagtcctg atccagttcc tg                                     22

<210> SEQ ID NO 7
<211> LENGTH: 20
<212> TYPE: DNA
<213> ORGANISM: Artificial Sequence
<220> FEATURE:
<223> OTHER INFORMATION: reverse primer for il-6

<400> SEQUENCE: 7
tgagttgtca tgtcctgcag                                        20

<210> SEQ ID NO 8
<211> LENGTH: 20
<212> TYPE: DNA
<213> ORGANISM: Artificial Sequence
<220> FEATURE:
<223> OTHER INFORMATION: forward primer for il-8

<400> SEQUENCE: 8
gtgcagtttt gccaaggagt                                        20

```
<210> SEQ ID NO 9
<211> LENGTH: 20
<212> TYPE: DNA
<213> ORGANISM: Artificial Sequence
<220> FEATURE:
<223> OTHER INFORMATION: reverse primer for il-8

<400> SEQUENCE: 9
aatttctgtg ttggcgcagt                                               20

<210> SEQ ID NO 10
<211> LENGTH: 20
<212> TYPE: DNA
<213> ORGANISM: Artificial Sequence
<220> FEATURE:
<223> OTHER INFORMATION: forward primer for inos

<400> SEQUENCE: 10
caccatcctg gtggaactct                                               20

<210> SEQ ID NO 11
<211> LENGTH: 20
<212> TYPE: DNA
<213> ORGANISM: Artificial Sequence
<220> FEATURE:
<223> OTHER INFORMATION: reverse primer for inos

<400> SEQUENCE: 11
tccaggatac cttggaccag                                               20

<210> SEQ ID NO 12
<211> LENGTH: 20
<212> TYPE: DNA
<213> ORGANISM: Artificial Sequence
<220> FEATURE:
<223> OTHER INFORMATION: forward primer for beta actin

<400> SEQUENCE: 12
agaaaatctg gcaccacacc                                               20

<210> SEQ ID NO 13
<211> LENGTH: 20
<212> TYPE: DNA
<213> ORGANISM: Artificial Sequence
<220> FEATURE:
<223> OTHER INFORMATION: reverse primer for beta actin

<400> SEQUENCE: 13
ggggtgttga aggtctcaaa                                               20
```

ANTI-INFLAMMATORY PEPTIDES AND COMPOSITION COMPRISING THE SAME

CROSS REFERENCE TO RELATED APPLICATIONS

This application is a divisional application of U.S. application Ser. No. 15/343,502, filed on Nov. 4, 2016, which is a divisional application of U.S. application Ser. No. 14/400,291, filed Mar. 2, 2015, which is a U.S. National Stage of International Application No. PCT/EP2013/059460, filed May 7, 2013, said International Application No. PCT/EP2013/059460 claims the benefit of Korean Application Nos. KR 10-2012-0104207 and KR 10-2012-0104144 filed on Sep. 19, 2012; Korean Application No. KR 10-2012-0071989 filed on Jul. 2, 2012; Korean Application Nos. KR 10-2012-0050533 and KR 10-2012-0050529 filed on May 11, 2012; and International Application No. PCT/EP2013/055329 filed on Mar. 15, 2012, all of which are herein incorporated by reference.

FIELD OF THE INVENTION

The present invention relates to anti-inflammatory peptides and compositions comprising the same.

REFERENCE TO SEQUENCE LISTING SUBMITTED ELECTRONICALLY VIA EFS-WEB

The content of the electronically submitted sequence listing (Name: 2473_0760007_Sequence listing ST25.txt; 3,284 bytes; and Date of Creation: Sep. 11, 2018) was originally submitted in the International Application No. PCT/EP2013/059460 and is incorporated herein by reference in its entirety.

BACKGROUND OF THE INVENTION

Inflammation is a type of biological defense as a means of protecting the body from damage of biological tissues that could be caused by external physical stimuli, chemical stimuli such as exposure to various allergens, or invasion of microorganisms including bacteria, fungi and viruses.

The Cyclooxygenase (COX) pathway or Lipoxygenase (LOX) Pathway can used for signaling inflammation, which produce prostaglandin, thromboxane, etc. Once the inflammatory signal is delivered, one of many changes that happen in the body is the expansion of the blood vessel for increased blood supply around the inflammation to concentrate blood cells such as neutrophils required for the inflammatory response. However, inflammatory diseases can result if an abnormal biological defense response occurs excessively. To prevent this, drugs that suppress excessive inflammatory responses by repressing enzymes used in inflammatory signaling pathway (for example, COX-1, COX-2, 5-LOX, 12-LOX etc.) are under development.

According to response time, inflammation is categorized as acute inflammation (immediate response, non-specific response, several days to several weeks), chronic inflammation (delayed response, specific response, several weeks or more), subacute inflammation (a middle stage in between acute inflammation and chronic inflammation, characteristics of mixed product of mononuclear and polymorphounuclear).

Also, aside from peptide factors, factors such as prostaglandin, leukotriene, lipid factors including platelet activating factor (PAF), synthetic enzyme of inflammation factor, free radical such as NO (nitric oxide), many kinds of cell adhesion molecules, the immune system, and coagulation factors can cause inflammation.

Once a cell is damaged due to the known causative agents of inflammation such as external biological factors (microbes, viruses, parasites), physical factors (mechanical stimuli, heat, radiation, electricity), and chemical factors, histamine and kinin are released. The released histamine and kinin will result in angiectasis, increased capillary permeability and concentration of macrophages at the inflammation site, and it causes increased blood flow rate, edema, immunocyte and antibody migration, pain and heat generation.

Currently used treatments for inflammation are synthetic drugs such as ibuprofen, antihistamines, steroids, cortisone, immunosuppressive agents, and immune agonist; those which only temporarily alleviate inflammation. These drugs do not fundamentally cure inflammation, and they have side effects such as hypersensitivity reaction, and deterioration of immune system, Therefore, for effective alleviation of inflammation, research is conducted to develop a substance that inhibits expression of the above mentioned inflammatory proteins. However, problems have arisen in anti-inflammation substances that had been developed previously. Diverse categories of anti-inflammatory drugs including Non-steroidal Anti-inflammatory Drugs (NSAIDs) and Steroidal Anti-inflammatory Drugs (SAIDs) have been developed; but not only do these drugs often bear side effects upon use, they also do not fundamentally cure the inflammation. Thus, there is a current need for anti-inflammatory drugs that are both physically and economically feasible. As one example, in acute or chronic inflammations such as chronic rheumatoid arthritis, not only do non-steroidal anti-inflammatory drugs suppress COX-2 enzyme activity, they are also known to suppress COX-1 activity, causing side effects such as gastrointestinal disorders.

The present invention was completed as present inventors have found that peptides derived from telomerase can have anti-inflammatory properties.

Therefore the objective of this invention is to provide a novel peptide.

Another objective of present invention is to provide the polynucleotide that codes the novel peptide.

Another objective of present invention is to provide a peptide that has anti-inflammatory activity.

Another objective of present invention is to provide an anti-inflammatory composition that uses this peptide as an active ingredient.

Another objective of present invention is to provide a cosmetic composition that uses this peptide as an active ingredient.

Another objective of present invention is to provide a pharmaceutical composition that uses this peptide as an active ingredient.

SUMMARY OF THE INVENTION

In one embodiment of the present invention, a peptide with anti-inflammatory activity, wherein the peptide comprises of amino acid sequence of SEQ ID NO: 1, or where the peptide has at least 80% homology with the amino acid sequence with SEQ ID NO: 1, or the peptide is a fragment of the above-mentioned peptides, is provided.

In another embodiment, the above-mentioned fragment consists of 3 or more amino acids. For instance, the fragment may consist of 4, 5, 6, 7, 8, 9, 10, 11, 12, 13, 14, or 15, 16, 17, 18, 19, 20, 21, 22, 23, 24, 25, or 26 amino acid residues.

In another embodiment, the above-mentioned peptide consists of 30 or less amino acids.

In another embodiment, the above-mentioned peptide consists of amino acid sequence of SEQ ID NO: 1. For instance, the peptide may consist of 29, 28, 27, 26, 25, 24, 23, 22, 21, 20, 19, 18, 17, 16, 15, 14, 13, 12, 11, 10, 9, or 8 amino acid residues.

In another embodiment, the above-mentioned peptide originates from human telomerase.

In one embodiment of the present invention, a polynucleotide encoding a peptide with anti-inflammatory activity, wherein the peptide comprises amino acid sequence of SEQ ID NO: 1, or the peptide has at least 80% sequence identity with SEQ ID NO: 1, or the peptide is a fragment of above-mentioned peptides, is provided.

In another embodiment of the polynucleotide, the above-mentioned fragment is made of at least 3 amino acids. For instance, the fragment may consist of 4, 5, 6, 7, 8, 9, 10, 11, 12, 13, 14, or 15, 16, 17, 18, 19, 20, 21, 22, 23, 24, 25, or 26 amino acid residues.

In another embodiment of the polynucleotide, the above-mentioned peptide consists of 30 or less amino acids. For instance, the peptide may consist of 29, 28, 27, 26, 25, 24, 23, 22, 21, 20, 19, 18, 17, 16, 15, 14, 13, 12, 11, 10, 9, or 8 amino acid residues.

In another embodiment of the polynucleotide, the above-mentioned peptide consists of an amino acid sequence of SEQ ID NO: 1.

In another embodiment of the polynucleotide, the above-mentioned peptide originates from human telomerase.

In one embodiment of the present invention, anti-inflammatory composition comprising a peptide as active ingredient, wherein the peptide comprises of amino acid sequence of SEQ ID NO: 1, the peptide has above 80% homology of amino acid sequence with SEQ ID NO: 1, or the peptide is a fragment of the above-mentioned peptides, is provided.

In another embodiment of the composition, the above-mentioned peptide consists of at least 3 amino acids, cf. above.

In another embodiment of the composition, the above-mentioned peptide consists of 30 or less amino acids, cf. above.

In another embodiment of the composition, the above-mentioned peptide consists of an amino acid sequence of SEQ ID NO: 1.

In another embodiment of the composition, the above-mentioned peptide originates from human telomerase.

In another embodiment of the composition, the above-mentioned composition is for treatment or prophylaxis of inflammatory disease.

In another embodiment of the composition, the above-mentioned composition is a cosmetic composition for improving or preventing skin inflammation.

In another embodiment of the composition, the above-mentioned composition is a pharmaceutical composition for treatment or prophylaxis of inflammatory disease.

In another embodiment of the composition, the above-mentioned composition is a food composition for treatment or prophylaxis of inflammation.

In another embodiment of the composition, the above-mentioned inflammatory disease is characterized by selecting from the group consisting of (1) general or localized inflammatory disease (for example, allergies; immune-complex disease; hayfever; hypersensitive shock; endotoxin shock; cachexia, hyperthermia; granulomatosis; or sarcoidosis); (2) gastrointestinal related diseases (for example, appendicitis; gastric ulcer; duodenal ulcer; peritonitis; pancreatitis; ulcerative, acute, or ischemic colitis; cholangitis; cholecystitis, steatorrhea, hepatitis, Crone's disease; or Whipple's Disease); (3) dermal related diseases (for example, psoriasis; burns; sunburns; dermatitis; Urticarial warts or wheal); (4) vascular related diseases (for example, angiitis; vasculitis; endocarditis; arteritis; atherosclerosis; thrombophlebitis; pericarditis; congestive heart failure; myocarditis; myocardial ischemia; periarteritis nodosa; recurrent stenosis; Buerger's disease; or rheumatic fever); (5) respiratory diseases (for example, asthma; epiglottitis; bronchitis; emphysema; rhinitis; cystic fibrosis; interstitial pneumonitis; COPD (chronic obstructive pulmonary disease); adult respiratory distress syndrome; coniosis; alveolitis; bronchiolitis; pharyngitis; pleurisy; or sinusitis); (6) bone, joint, muscle and connective tissue related diseases (for example, eosinophilic granuloma; arthritis; arthralgia; osteomyelitis; dermatomyositis; fasciitis; Paget's disease; gout; periodontal disease; rheumatoid arthritis; myasthenia gravis; ankylosing spondylitis; or synovitis); (7) urogenital disorders (for example, epididymitis; vaginitis; prostatitis; or urethritis); (8) central or peripheral nervous system related diseases (for example, Alzheimer's disease; meningitis; encephalitis; multiple sclerosis; cerebral infarction; cerebral embolism; Guillain-Barre syndrome; neuritis; neuralgia; spinal cord injury; paralysis; or uveitis); (9) virus (for example, influenza; respiratory syncytial virus; HIV; hepatitis B; hepatitis C; or herpes virus), infectious disease (for example, Dengue fever; or septicemia), fungal infection (for example, candidiasis); or bacterial, parasitic, and similar microbial infection (for example, disseminated bacteremia; malaria; onchocerciasis; or amebiasis); (10) autoimmune disease (for example, thyroiditis; lupus; Goodpasture's syndrome; allograft rejection; graft versus host disease; or diabetes); and (11) cancer or tumor disease (for example, Hodgkin's disease).

In one embodiment of the present invention, a method for treating or preventing inflammatory diseases by administering the anti-inflammatory composition is provided.

In one embodiment of the present invention, a kit for prophylaxis or treatment of inflammatory disease comprising: a peptide with anti-inflammatory activity or a composition comprising the peptide, wherein the peptide comprises amino acid sequence of SEQ ID NO: 1, the peptide has above 80% amino acid sequence homology with SEQ ID NO: 1, or the peptide is a fragment of above-mentioned peptides; and instructions including at least one of administration dose, administration route, administration frequency, and indication of the peptide or composition, is provided.

INDUSTRIAL APPLICABILITY

According to the present invention, a peptide that has a sequence of SEQ ID NO: 1 has outstanding efficacy in both suppressing inflammation and in prophylactic means. Therefore, the composition comprising the peptides of this invention can be used as anti-inflammatory pharmaceutical composition or as cosmetic composition, in turn, treating and preventing a variety of different types of inflammatory diseases.

REFERENCE

KR2012-0130996A
KR2012-0133661A

KR2011-0060940A
US2011-0150873A1
Bonaldi T et al., EMBO J, (22)5551-60, 2003
Yankner B A et al, Science (New York, N.Y.) [1990, 250 (4978): 279-282]
Dahlgren K N et al, J. Biol. Chem. 277: 32046-32053, 2002.

BRIEF DESCRIPTION OF THE DRAWINGS

FIG. 3 represents the inhibition levels of cytokines in THP1 cell line which were treated with none, LPS, PEP 1 and LPS+PEP 1.

FIG. 4 represents viability of neural stem cell treated with 0, 2.5, 5.0, 10, 20 and 40 μM of amyloid-β protein.

FIG. 5 represents proliferation of neural stem cell treated with 0, 2.5, 5.0, 10, 20 and 40 μM amyloid-β protein.

FIG. 6 represents viability of neural stem cell treated with 0, 1, 10, 50, 100 and 200 μM of PEP 1.

DETAILED DESCRIPTION OF THE INVENTION

Figure 1:
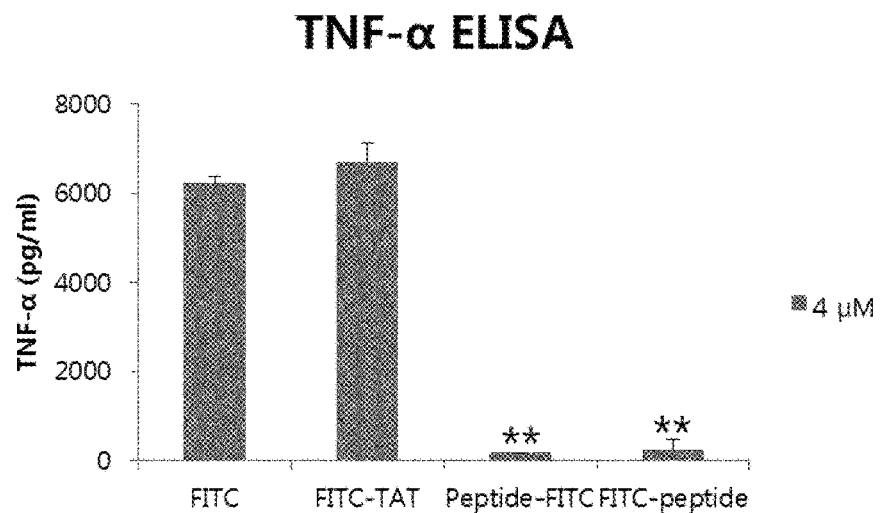
FIG. 1 is a graph which shows the results of performing TNF-α ELISA with the culture of monocytes derived from PBMC. The monocytes were stimulated with LPS (10 ng/ml) for two hours, then reacted with each peptide, FITC, FITC-TAT, PEP 1-FITC and FITC-peptide for two hours. (**$P<0.01$. Compared with the negative control (FITC and FITC-TAT).

Since the present invention can have adaptability for diverse transformation and examples of practical application, below is a more detailed description of the present invention. Nevertheless, this is no means to limit the form of practical application; it should be understood that the intention is to include the concept and the extent of technology in all of the transformation, equivalents to alternatives. In describing the present invention, if any detailed description about the prior art is considered to deteriorate the fundamental principles of the present invention, the description will be omitted.

A telomere is known as a repetitive sequence of genetic material at the ends of chromosomes that prevent chromosomes from damage or merging of other chromosomes. The length of a telomere is shortened at each cell division, and after a certain number of cell division, the telomere length is extremely shortened to the extent in which the cell stops dividing and dies. On the other hand, the elongation of telomeres is known to extend the life span of a cell. For an example, cancer cells excrete an enzyme called telomerase, which prevents shortening of telomeres, thus resulting in proliferation of cancer cells. The present invention was accomplished upon the discovery of telomerase-derived peptides with anti-inflammatory effects.

In one embodiment of the present invention, a peptide with anti-inflammatory activities is provided. The peptide comprises at least one amino acid sequence of SEQ ID NO: 1, the peptide has above 80% homology with above-mentioned sequence, or the peptide is a fragment of the above-mentioned peptides.

Peptide with anti-inflammatory activity in the present invention is a peptide having an amino acid sequence to SEQ ID NO: 1. Peptide of SEQ ID NO: 1 is a peptide consisting of 16 amino acids in the location of telomerase-[611-626].

SEQ ID NO: 1 EARPALLTSRLRFIPK

In one embodiment of the present invention, a polynucleotide that codes a peptide with anti-inflammatory activities is provided. The polynucleotide codes a peptide comprising at least one amino acid sequence of SEQ ID NO: 1, a peptide having above 80% homology with above-mentioned sequence, or a peptide being a fragment of the above-mentioned peptides. The polynucleotide mentioned above enables production of the peptides in large quantities. For example, cultivation of vectors that include polynucleotides encoding peptides allows production of peptides in large quantities.

The peptides disclosed herein can include a peptide comprising amino acid sequence above 80%, above 85%, above 90%, above 95%, above 96%, above 97%, above 98%, or above 99% homology. Moreover, the peptides disclosed in the present invention can include a peptide comprising SEQ ID NO: 1 or its fragments, and a peptide with more than 1 transformed amino acid, more than 2 transformed amino acid, more than 3 transformed amino acid, more than 4 transformed amino acid, more than 5 transformed amino acid, more than 6 transformed amino acid, or more than 7 transformed amino acid.

In the present specification and claims, the terms "homology" and "sequence identity" are used interchangeably to indicate the degree of sequence overlap between two amino acid (or if relevant: nucleic acid) sequences.

Unless otherwise stated the term "Sequence identity" for peptides as used herein refers to the sequence identity calculated as $(n_{ref}-n_{dif})\cdot 100/n_{ref}$, wherein $n_{dif}$ is the total number of non-identical residues in the two sequences when aligned so that a maximum number of amino acids are identical and wherein $n_{ref}$ is the number of residues in the shortest of the sequences. Hence, the DNA sequence agtcagtc will have a sequence identity of 75% with the sequence aatcaatc ($n_{dif}=2$ and $n_{ref}=8$).

In some embodiments the sequence identity is determined by conventional methods, e.g., Smith and Waterman, 1981, Adv. Appl. Math. 2:482, by the search for similarity method of Pearson & Lipman, 1988, Proc. Natl. Acad. Sci. USA 85: 2444, using the CLUSTAL W algorithm of Thompson et al., 1994, Nucleic Acids Res 22:467380, by computerized implementations of these algorithms (GAP, BESTFIT, FASTA, and TFASTA in the Wisconsin Genetics Software Package, Genetics Computer Group). The BLAST algorithm (Altschul et al., 1990, Mol. Biol. 215:403-10) for which software may be obtained through the National Center for Biotechnology Information www.ncbi.nlm.nih.gov/) may also be used. When using any of the aforementioned algorithms, the default parameters for "Window" length, gap penalty, etc., are used.

In one embodiment of the present invention, changes in amino acid sequence belong to the modification of peptide's physical and chemical characteristics. For example, amino acid transformation can be performed by improving thermal stability of the peptide, altering substrate specificity, and changing the optimal pH.

In one embodiment of the present invention, a peptide comprising amino acid sequence of SEQ ID NO: 1, a peptide comprising of amino acid sequence above 80% homology with above-mentioned sequence or a peptide fragment of above-mentioned peptides is preferably made of 30 or less amino acids.

In one embodiment of the present invention, a peptide comprising amino acid sequence of SEQ ID NO: 1, a peptide comprising of amino acid sequence above 80% homology with above-mentioned sequence or a peptide fragment of above-mentioned peptides comprises a peptide originates from telomerase, more specifically, telomerase of *Homo sapiens*.

The term "amino acid" herein includes not only the 22 standard amino acids that are naturally integrated into peptide but also the D-isomers and transformed amino acids. Therefore, in a specific embodiment of the present invention, a peptide herein includes a peptide having D-amino acids. On the other hand, a peptide may include non-standard amino acids such as those that have been post-translationally modified. Examples of post-translational modification include phosphorylation, glycosylation, acylation (including acetylation, myristorylation, plamitoylation), alkylation, carboxylation, hydroxylation, glycation, biotinylation, ubiquitinylation, transformation in chemical properties (e.g. β-removing deimidation, deamidation) and structural transformation (e.g. formation of disulfide bridge). Also, changes of amino acids are included and the changes of amino acids occur due to chemical reaction during the combination process with crosslinkers for formation of a peptide conjugate.

A peptide disclosed herein may be a wild-type peptide that has been identified and isolated from natural sources. On the other hand, when compared to peptide fragments of SEQ ID NO: 1, the peptides disclosed herein may be artificial mutants that comprise one or more substituted, deleted and/or inserted amino acids. Amino acid alteration in wild-type polypeptide—not only in artificial mutants—comprises conservative substitution of amino acids that do not influence protein folding and or activation. Examples of conservative substitution belong to the group consisting of basic amino acids (arginine, lysine and histidine), acidic amino acids (glutamic acid and aspartic acid), polar amino acids (glutamine and asparagines), hydrophobic amino acids (leucine, isoleucine, valine and methionine), aromatic amino acids (phenylalanine, tryptophan and tyrosine), and small amino acids (glycine, alanine, serine, and threonine). The amino acid substitutions that do not generally alter the specific activity are known in the art of the present invention. Most common occurred alteration are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, Asp/Gly, and the opposite alterations. Another example of conservative substitutions are shown in the following table 1.

TABLE 1

| Original amino acid | Examples of residue substitution | Preferable residue substitution |
| --- | --- | --- |
| Ala (A) | val; leu; ile | Val |
| Arg (R) | lys; gln; asn | Lys |
| Asn (N) | gln; his; asp, lys; arg | Gln |
| Asp (D) | glu; asn | Glu |
| Cys (C) | ser; ala | Ser |
| Gln (Q) | asn; glu | Asn |
| Glu (E) | asp; gln | Asp |
| Gly (G) | ala | Ala |
| His (H) | asn; gln; lys; arg | Arg |
| Ile (I) | leu; val; met; ala; phe; norleucine | Leu |
| Leu (L) | norleucine; ile; val; met; ala; phe | Ile |
| Lys (K) | arg; gln; asn | Arg |
| Met (M) | leu; phe; ile | Leu |
| Phe (F) | leu; val; ile; ala; tyr | Tyr |
| Pro (P) | ala | Ala |
| Ser (S) | thr | Thr |
| Thr (T) | ser | Ser |
| Trp (W) | tyr; phe | Tyr |

TABLE 1-continued

| Original amino acid | Examples of residue substitution | Preferable residue substitution |
|---|---|---|
| Tyr (Y) | trp; phe; thr; ser | Phe |
| Val (V) | ile; leu; met; phe; ala; norleucine | Leu |

The substantial transformation of the biological properties of peptides are performed by selecting significantly different substitution in the following efficacies: (a) the efficacy in maintaining the structure of the polypeptide backbone in the area of substitution, such as sheet or helical three-dimensional structures, (b) the efficacy in maintaining electrical charge or hydrophobicity of the molecule in the target area, or (c) the efficacy of maintaining the bulk of the side chain. Natural residues are divided into groups by general side chain properties as the following:
  (1) hydrophobicity: Norleucine, met, ala, val, leu, ile;
  (2) neutral hydrophilicity: cys, ser, thr;
  (3) acidity: asp, glu;
  (4) basicity: asn, gln, his, lys arg;
  (5) residue that affects chain orientation: gly, pro; and
  (6) aromaticity: trp, tyr, phe.

Non-conservative substitutions may be performed by exchanging a member of the above classes to a different class's. Any cysteine residues that are not related in maintaining the proper three-dimensional structure of the peptide can typically be substituted into serine, thus increasing the oxidative stability of the molecule and preventing improper crosslinkage. Conversely, improvement of stability can be achieved by adding cysteine bond(s) to the peptide.

Altered types of amino acids variants of peptides are those that antibody glycosylation pattern changed. The term "change" herein relates to deletion of carbohydrate residues and/or addition of at least one glycosylated residues that do not exist within a peptide.

Glycosylation in peptides are typically N-connected or O-connected. The term "N-connected" herein relates to that carbohydrate residues are attached to the side chain of asparagine residues. As tripeptide sequences, asparagine-X-serine and asparagine-X-threonine (where the X is any amino acid except proline) are the recognition sequence for attaching carbohydrate residue enzymatically to the side chain of asparagine. Therefore, with the presence of one of these tripeptide sequences in a polypeptide, the potential glycosylation sites are created. "O-connected glycosylation" means attaching one of sugar N-acetylgalactosamine, galactose, or xylose to hydroxyl amino acids. The hydroxyl amino acids are most typically serine or threonine, but 5-hydroxyproline or 5-hydroxylysine can be used.

Addition of glycosylation site to a peptide is conveniently performed by changing amino acid sequence to contain tripeptide sequence mentioned above (for N-linked glycosylation sites). These changes may be made by addition of at least one serine or threonine residues to the first antibody sequence, or by substitution with those residues (for O-linked glycosylation sites).

In one embodiment of the present invention, a polynucleotide is a nucleic acid molecule that can be spontaneous or artificial DNA or RNA molecules, either single-stranded or double-stranded. The nucleic acid molecule can be one or more nucleic acids of same type (for example, having a same nucleotide sequence) or nucleic acids of different types. The nucleic acid molecules comprise one or more DNA, cDNA, decoy DNA, RNA, siRNA, miRNA shRNA, stRNA, snoRNA, snRNA PNA, antisense oligomer, plasmid and other modified nucleic acids, but not limited to those.

A HMGB1 protein is known as a cytokine. It first undergoes acetylation and translocation to cytoplasm by external stimulation. Then it is secreted out of the cell, therefore serving the role of inflammation-causing cytokine. Because when one has an inflammation due to such activity, HMGB1 protein is secreted out of the cell, and patients with inflammatory diseases such as Churg strauss syndrome, rheumatoid arthritis and Sjogren's syndrome will present with elevated serum levels of HMGB1. Hence, if nucleus contains large amount of HMGB1 even when there is a stimulus that causes inflammation, it is suggestive of the fact that HMGB1 is not being secreted out of the cell, which means inflammation is being suppressed.

In one embodiment of the present invention, when treated a cell with a peptide comprising amino acid sequence of SEQ ID NO: 1, a peptide having above 80% homology of amino acid sequence with above-mentioned sequence, or a fragment of the above-mentioned peptides, amount of HMGB1 within the nucleus increases. This represents that the peptides mentioned above have excellent inflammation preventive or suppressive effects.

Also, in specific embodiments of the present invention, a peptide comprising amino acid sequence of SEQ ID NO: 1, a peptide having above 80% homology of amino acid sequence with above-mentioned sequence, or a fragment of the above-mentioned peptides, has an advantage in that it has high feasibility due to its low toxicity within a cell.

In the present invention, an "inflammatory disease" is a broad indication that refers to any disease that designates inflammation as a main cause or inflammation caused by disease. Specifically, an inflammatory disease includes (1) general or localized inflammatory disease (for example, allergies; immune-complex disease; hayfever; hypersensitive shock; endotoxin shock; cachexia, hyperthermia; granulomatosis; or sarcoidosis); (2) gastro-intestinal related diseases (for example, appendicitis; gastric ulcer; duodenal ulcer; peritonitis; pancreatitis; ulcerative, acute, or ischemic colitis; cholangitis; cholecystitis, steatorrhea, hepatitis, Crone's disease; or Whipple's Disease); (3) dermal related diseases (for example, psoriasis; burns; sunburns; dermatitis; Urticarial warts or wheal); (4) vascular related diseases (for example, angiitis; vasculitis; endocarditis; arteritis; atherosclerosis; thrombophlebitis; pericarditis; congestive heart failure; myocarditis; myocardial ischemia; periarteritis nodosa; recurrent stenosis; Buerger's disease; or rheumatic fever); (5) respiratory diseases (for example, asthma; epiglottitis; bronchitis; emphysema; rhinitis; cystic fibrosis; interstitial pneumonitis; COPD (chronic obstructive pulmonary disease); adult respiratory distress syndrome; coniosis; alveolitis; bronchiolitis; pharyngitis; pleurisy; or sinusitis); (6) bone, joint, muscle and connective tissue related diseases (for example, eosinophilic granuloma; arthritis; arthralgia; osteomyelitis; dermatomyositis; fasciitis; Paget's disease; gout; periodontal disease; rheumatoid arthritis; myasthenia gravis; ankylosing spondylitis; or synovitis); (7) urogenital disorders (for example, epididymitis; vaginitis; prostatitis; or urethritis); (8) central or peripheral nervous system related diseases (for example, Alzheimer's disease; meningitis; encephalitis; multiple sclerosis; cerebral infarction; cerebral embolism; Guillain-Barre syndrome; neuritis; neuralgia; spinal cord injury; paralysis; or uveitis); (9) virus (for example, influenza; respiratory syncytial virus; HIV; hepatitis B; hepatitis C; or herpes virus), infectious disease (for example, Dengue fever; or septicemia), fungal infection (for example, candidiasis); or bacterial, parasitic, and similar microbial infection (for example, disseminated bacteremia; malaria; onchocerciasis; or amebiasis); (10) autoimmune disease (for example, thyroiditis; lupus; Goodpasture's syndrome; allograft rejection; graft versus host disease; or diabetes); and (11) cancer or tumor disease (for example, Hodgkin's disease), but not limited to those.

Treating the inflammatory component of such diseases has been a major goal of the global pharmaceutical industry for a number of decades, and a wide variety of useful treatments have been developed. Examples include the corticosteroids (a range of natural, semisynthetic and synthetic agents designed to mimic the effect of Cortisol, including prednisolone, methylprednisolone, dexamethasone, betamethasone, fluticasone and so forth), cyclooxygenase inhibitors (both non-selective or cox-1 selective, such as indomethacin, sulfasalzine and aspirin, and more recently cox-2 selective, such as celecoxib), leukotriene blockers (such as monteleukast) and anti-TNFs (such as modified monoclonal neutralising antibodies, including infliximab (Remicade™) and adalimumab (Humira™), TNF receptor fusion proteins, such as etanercept (Enbrel™), as well as small molecule TNF-α synthesis inhibitors like thalidomide).

In one embodiment of the present invention, an anti-inflammatory composition comprising a peptide as an active ingredient is provided. The peptide comprises amino acid sequence of SEQ ID NO: 1, the peptide has above 80% homology with above-mentioned sequence, or the peptide is a fragment of the above-mentioned peptides.

In one embodiment of the present invention, the anti-inflammatory composition may contain 0.1 μg/mg to 1 mg/mg, specifically 1 μg/mg to 0.5 mg/mg, more specifically 10 μg/mg to 0.1 mg/mg of a peptide comprising of amino acid sequence SEQ ID NO: 1, a peptide comprising of amino acid sequence above 80% homology with above-mentioned sequence, or peptide fragment of above-mentioned peptides. When the peptide is contained in the above mentioned range, all the safety and stability of the composition may be satisfied and appropriate in terms of cost-effectiveness.

In one embodiment of the present invention, the composition may have application with all animals including human, dog, chicken, pig, cow, sheep, guinea pig, and monkey.

In one embodiment of the present invention, the pharmaceutical composition for the use of treatment or prophylaxis of inflammatory disease with an active ingredient that is comprised of a peptide consisting of an amino acid of SEQ ID NO: 1, a peptide comprising of amino acid sequence above 80% homology with above-mentioned sequence, or peptide fragment of SEQ ID NO: 1, is provided. In one embodiment of the present invention, the pharmaceutical composition may be administered through oral, rectal, transdermal, intravenous, intramuscular, intraperitoneal, in the bone marrow, epidural or subcutaneous means.

Forms of oral administration may be, but not limited to, tablets, pills, soft or hard capsules, granules, powders, solution, or emulsion. Forms of non-oral administration may be, but not limited to, injections, drips, lotions, ointments, gels, creams, suspensions, emulsions, suppository, patch, or spray.

In one embodiment of the present invention, the pharmaceutical composition, if necessary, may contain additives, such as diluents, excipients, lubricants, binders, disintegrants, buffers, dispersants, surfactants, coloring agents, aromatics or sweeteners. In one embodiment of the present invention, the pharmaceutical composition can be manufactured by conventional methods of the industry in the art.

In one embodiment of the present invention, the active ingredient of the pharmaceutical composition may vary according to the patient's age, sex, weight, pathology and state, administration route, or prescriber's judgment. Dosage based on these factors is determined within levels of those skilled in the art, and the daily dose for example may be, but not limited to, 0.1 μg/kg/day to 1 g/kg/day, specifically 1 μg/kg/day to 10 mg/kg/day, more specifically the 10 μg/kg/day to 1 mg/kg/day, more specifically the 50 μg/kg/day to 100 μg/kg/day. In one embodiment of the present invention, the pharmaceutical composition may be administered, but not limited to, 1 to 3 times a day.

In one embodiment of the present invention, a skin external composition for improvement or prevention of skin inflammation is provided. The skin external composition may contain an active ingredient that is a peptide comprising of an amino acid sequence of SEQ ID NO: 1, a peptide comprising of amino acid sequence above 80% homology with above-mentioned sequence, or a peptide fragment of above-mentioned peptides.

In another embodiment of the present invention, a cosmetic composition for improvement or prevention of skin inflammation is provided. The cosmetic composition may contain an active ingredient that is a peptide comprising of an amino acid sequence of SEQ ID NO: 1, a peptide comprising of amino acid sequence above 80% homology with above-mentioned sequence, or peptide fragment of above-mentioned peptides.

In one embodiment of the present invention, external application composition or cosmetic composition may be provided in all forms appropriate for topical applications. For example, forms can be provided as solutions, emulsions obtained by dispersion of oil phase in water, emulsion obtained by dispersion of water in oil phase, suspension, solid, gel, powder, paste, foam or aerosol. These forms can be manufactured by conventional methods of the industry in the art.

In one embodiment of the present invention, the cosmetic composition may include, within levels that will not harm the main effect, other ingredients that can desirably increase the main effect. In one embodiment of the present invention, the cosmetic composition may additionally include moisturizer, emollient agents, surfactants, UV absorbers, preservatives, fungicides, antioxidants, pH adjusting agent, organic or inorganic pigments, aromatics, cooling agent or antiperspirant. The formulation ratio of the above-mentioned ingredients can be decided by those skilled in the art within levels that will not harm the purpose and the effects of the present invention, and the formulation ratio based on total weight of the cosmetic composition can be 0.01 to 5% by weight, specifically 0.01 to 3% by weight.

In one embodiment of the present invention, a food composition for inflammation prevention or suppression is provided. The food composition may contain with an active ingredient that is a peptide comprising of an amino acid sequence of SEQ ID NO: 1, a peptide comprising of amino acid sequence above 80% homology with above-mentioned sequence, or peptide fragment of above-mentioned peptides.

In one embodiment of the present invention, food composition is not limited to forms, but for example may be granules, powder, liquid, and solid forms. Each form can be formed with ingredients commonly used in the industry appropriately chosen by those skilled in the art, in addition to the active ingredient, and can increase the effect with other ingredients.

Decision for dosage on the above-mentioned active ingredient is within the level of those skilled in the art, and daily dosage for example may be 1 μg/kg/day to 10 mg/kg/day, more specifically the 10 μg/kg/day to 1 mg/kg/day, more specifically the 50 μg/kg/day to 100 μg/kg/day, but not limited to these numbers and can vary according to age, health status, complications and other various factors.

In one embodiment of the present invention, a use of prevention or treatment of inflammatory disease with a peptide comprising of an amino acid sequence of SEQ ID NO: 1, a peptide comprising of amino acid sequence above 80% homology with above-mentioned sequence, or peptide fragment of above-mentioned peptides, is provided.

In one embodiment of the present invention, the method of prevention or treatment of inflammatory disease with applying peptides mentioned above in patients is provided.

In one embodiment of the present invention, a kit for prophylaxis or treatment of inflammatory diseases is provided. The kit may contain: a peptide with anti-inflammatory activity or a composition comprising of the peptide, wherein the peptide comprises amino acid sequence of SEQ ID NO: 1, the peptide has above 80% homology with above-mentioned sequence, or the peptide is a fragment of the above-mentioned peptides; and instructions including at least one of administration dose, administration route, administration frequency, and indication of the peptide or composition.

The terms used herein is intended to be used to describe the embodiments, not to limit the present invention. Terms without numbers in front are not to limit the quantity but to show that there may be more than one thing of the term used. The term "including", "having", "consisting", and "comprising" shall be interpreted openly (i.e. "including but not limited to").

Mention of range of numbers is used instead of stating separate numbers within the range, so unless it is explicitly stated, each number can be read as separate numbers integrated herein. The end values of all ranges are included in the range and can be combined independently.

Unless otherwise noted or clearly contradicting in context, all methods mentioned herein can be performed in the proper order. The use of any one embodiment and all embodiment, or exemplary language (e.g., that use "like~"), unless included in the claims, is used to more clearly describe the present invention, not to limit the scope of the present invention. Any language herein outside of the claims should not be interpreted as a necessity of the present invention. Unless defined otherwise, technical and scientific terms used herein have meaning normally understood by a person skilled in the art that the present invention belongs to.

The preferred embodiments of the present invention are the best mode known to the inventors to perform the present invention. It may become clear to those skilled in the art after reading the statements ahead of the variations in the preferred embodiments. The present inventors hope that those skilled in the art can use the variations adequately and present invention be conducted in other ways than listed herein. Thus, the present invention, as allowed by the patent law, includes equivalents, and variations thereof, of the key points of the invention stated in the appended claims. In addition, all possible variations within any combination of the above-mentioned components are included in the present invention, unless explicitly stated otherwise or contradicting in context. Although the present invention is described and shown by exemplary embodiments, those skilled in the art will understand well that there can be various changes in the form and details without departing from the spirit of the invention and range, defined by the claims below.

Tumor necrosis factor (TNF), particularly TNF-α, is known to be released from inflammatory cells and cause various cytotoxic reactions, immunological reactions and inflammatory reactions. TNF-α is known to be involved in the occurrence and prolongation of many inflammatory and autoimmune diseases and further cause serious septicemia and septic shock when it is released into the blood and acts systemically. Because TNF-α is a factor associated widely with the immune system of a living body, the development of agents inhibiting TNF-α is actively carried out. TNF-α is biosynthesized in an inactive form and becomes an active form by being cleaved by protease; the enzyme responsible for the activation is called a tumor necrosis factor-converting enzyme (TACE). Thus, a substance inhibiting this TACE can treat, improve, or prevent diseases, pathologic conditions, abnormal conditions, troubles, adverse symptoms and the like ascribed to TNF-α (KR2011-0060940A).

High-mobility group box 1 (HMGB1) protein exists in high concentrations in thymus, lymph nodes, testes, and in fetal liver, and with exception to liver and brain cells, usually exists inside of the nucleus. The said HMGB1 protein has 3 domains consisting of A-box, B-box, and C-terminal.

It was reported by Tracey et al., 1999 that HMGB1 protein has a role as a cytokine which induces inflammation, and the mechanism of said HMGB1's inflammation induction is by an external stimulus causing acetylation of HMGB1 which then moves from the nucleus into the cytoplasm. Afterward, it is known to be secreted out of the cell, or secreted out from the cell in necrosis. (Bonaldi T et al., EMBO J, (22)5551-60, 2003).

The invention is further described by the figures, the following examples and experiments, which are solely for the purpose of illustrating specific embodiments of this invention, and are not to be construed as limiting the scope of the invention in any way.

Example 1

Synthesis of PEP-1 and Measurement of Anti-Inflammatory Activities of PEP-1 (SEQ ID NO: 1)

Experiment 1-1: Synthesis of PEP-1 (SEQ ID NO: 1)

A peptide comprised of 16 amino acids with the chemical structure 1 as below having the sequence SEQ ID: 1 (PEP-1) derived from human telomerase was synthesized:

<Chemical Structure 1>

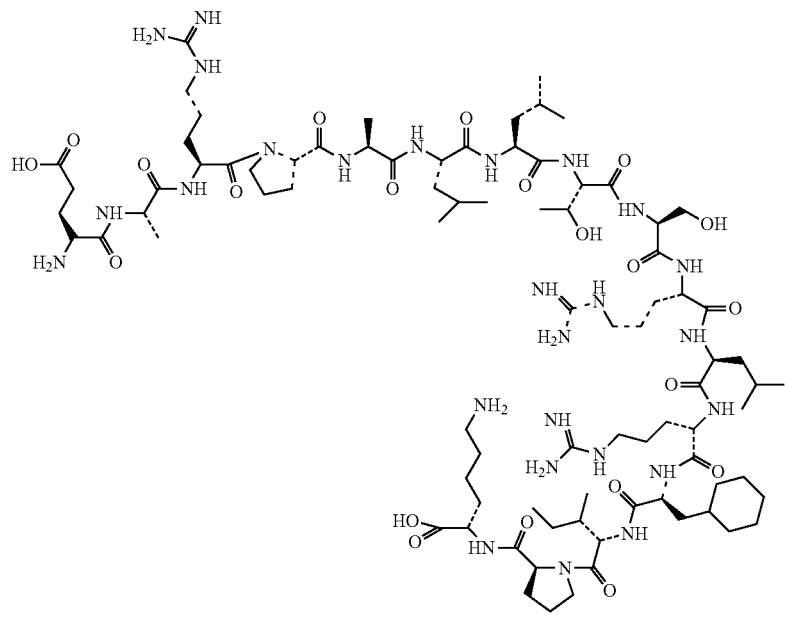

SEQ ID NO: 1 (PEP-1) was synthesized according to the existing method of solid phase peptide synthesis. In detail, the peptides were synthesized by coupling each amino acid from C-terminus through Fmoc solid phase peptide synthesis, SPPS, using ASP48S (Peptron, Inc., Daejeon ROK). Those peptides with their first amino acid at the C-terminus being attached to resin were used as follows:

$NH_2$-Lys(Boc)-2-chloro-Trityl Resin
$NH_2$-Ala-2-chloro-Trityl Resin
$NH_2$-Arg(Pbf)-2-chloro-Trityl Resin All the amino acid materials to synthesize the peptide were protected by Fmoc at the N-terminus, and the amino acid residues were protected by Trt, Boc, t-Bu (t-butylester), Pbf (2,2,4,6,7-pentamethyl dihydro-benzofuran-5-sulfonyl) that can be dissolved in acid. Such as: Fmoc-Ala-OH, Fmoc-Arg(Pbf)-OH, Fmoc-Glu(OtBu)-OH, Fmoc-Pro-OH, Fmoc-Leu-OH, Fmoc-Ile-OH, Fmoc-Phe-OH, Fmoc-Ser(tBu)-OH, Fmoc-Thr(tBu)-OH, Fmoc-Lys(Boc)-OH, Fmoc-Gln(Trt)-OH, Fmoc-Trp(Boc)-OH, Fmoc-Met-OH, Fmoc-Asn(Trt)-OH, Fmoc-Tyr(tBu)-OH, Fmoc-Ahx-OH, Trt-Mercaptoacetic acid.

HBTU[2-(1H-Benzotriazole-1-yl)-1,1,3,3-tetamethylaminium hexafluorophosphate]/HOBt [N-Hydroxybenzotriazole]/NMM [4-Methylmorpholine] were used as the coupling reagents. In 20% of DMF, piperidine was used to remove Fmoc. In order to remove the protection from residue or to separate the synthesized peptide from Resin, cleavage cocktail [TFA (trifluoroacetic acid)/TIS (triisopropylsilane)/EDT (ethanedithiol)/$H_2O$=92.5/2.5/2.5/2.5] was used.

Synthesized the peptide by using the solid phase scaffold combined to starting amino acid with the amino acid protection, reacting the corresponding amino acids separately, washing with solvent and deprotected, and repeating the process. After cutting off the synthesized peptide from the resin, it was purified by HPLC and verify for synthesis by MS, and then freeze-dried.

Specific synthesis process of PEP 1 is described by the following.

1) Coupling

Melted the amino acid (8 equivalent) protected with $NH_2$-Lys(Boc)-2-chloro-Trityl Resin, and coupling agent HBTU (8 equiv.)/HOBt (8 equiv.)/NMM (16 equiv.) and added to DMF, then let react in room temperature for 2 hours, then washed with DMF, MeOH, and DMF in that order.

2) Fmoc deprotection

Added 20% piperidine in DMF and reacted in room temperature for 5 minutes 2 times, then washed with DMF, MeOH, and DMF in that order.

3) Make the basic framework of peptide by repeating reactions 1 and 2 repeatedly.

4) Cleavage: Add Cleavage Cocktail to the completely synthesized peptide and separated the peptide from the resin.

5) Add cooling diethyl ether into obtained mixture, and then centrifugation is used to precipitate gathered peptide.

6) After purification by Prep-HPLC, check the molecular weight by LC/MS and lyophilize to produce in powder form.

Example 2

Anti-Inflammatory Activity Measurement of PEP-1

Cell Lines Culture

Raw 264.7macrophage cell (KCBL, 40071) from Korea Cell Bank was maintained in Dulbecco's modified Eagle's medium (DMEM; PAA, Austria) containing 10% fetal bovine serum (FBS; Gibco Laboratories), 100 unit/mL of streptomycin, and penicillin (Gibco Laboratories) at 37° C. with 5% CO. Raw264.7 cells were seeded into a 96-well plate at a density of $1\times10^6$ cells/mL and incubated overnight.

On the following day, the medium was replaced with fresh medium and 5 μg/mL of peptide (obtained as described in Experiment example 1) was added to the cells. After 30 min incubation of cells with the peptide 50 μL of LPS (to a final concentration of 1 μg/mL) was added, and cells were incubated for additional 24 hr. The experimental sample with the induction of inflammatory response was treated with 1 μg/mL mL lipopolysaccharide (LPS; Sigma, USA) and control sample was treated with phosphate buffered saline (PBS; pH 7.2). The supernatant samples from each condition was collected in eppendorf tubes and subjected to further analysis.

Experiment 2-1. NO Level Analysis

The level of nitric oxide (NO) was measured in Raw 264.7 cell ($1\times10^6$ cell/ml) using Griess reagent system (Promega, USA). Culture medium of 50 μl was added to a 96-well plate and Griess reagent I (NED) solution and Griess reagent II (Sulfanilamide solution) are added in the same amount. After 10 min incubation of cells with the reagents, the optical density at 540 nm was measured within 30 min using a microplate reader (Molecular Devices, USA). The concentration of NO was calculated by using a standard curve (0~100 μM) of sodium nitrite.

As shown in Table 2 below, stimulation of cells with LPS increased the expression of NO, but in co-treatment with LPS and PEP-1, the expression level of NO mentioned above decreased. NO is produced during inflammation, and the result showing PEP-1 reduced NO level to 65% of the control strongly support the anti-inflammatory effect of PEP-1.

TABLE 2

The measurement of anti-inflammatory effect of human telomerase derived PEP 1

| Test sample | | NO Expression Level of control (%) | Decreased NO Expression Level (%) |
|---|---|---|---|
| | PBS | 0 | — |
| LPS 1 μg/mL | PBS | 100 | 0 |
| | PEP 1 (0.5 μg/mL) | 35 | 65 |

Experiment 2-2. Analysis of Cytokine Inhibitory Effect

To investigate the effect of PEP-1 on inhibiting proinflammatory cytokine production RAW 264.7 cell were pretreated with PEP 1 at a concentration of 5 μg/mL challenged with LPS at a concentration of 1 μg/mL, and cells were further incubated for 24 hr. The supernatant samples containing cell culture medium was collected and analyzed for the cytokine levels using ELISA kits (eBioscience, San Diego).

96 wells plates were coated with 100 μL of capture antibodies (diluted in coating buffer to the concentration recommended by manufacturer's protocol) overnight at 4° C. Then, after washing the plates 5 times, 200 μL of assay diluents was added to each well and incubated for 1 hr at room temperature for blocking. After washing each well with wash buffer five times, cell culture sample or each cytokine standard protein sample was diluted and 100 μL of each added into each well. The plate containing samples were incubated overnight at 4° C. Then, after washing the plate five times with the wash buffer, 100 μL of secondary antibody conjugated to avidin was added and incubated for 1 hr at room temperature.

Following incubation with the secondary antibody, the plate was washed five times and incubated with 100 μL of avidin-HRP (BD Bioscience) for 30 min at room temperature. After washing the plate seven times, 100 μL of TMB solution (Pierce) was added and incubated for 15 min at room temperature. The reaction was stopped by adding 50 μl of 2N $H_2SO_4$ in each well The optical density at 450 nm was measured using a microplate reader. Statistical analysis was performed by variance analysis using ANOVA procedure of SPSS program, and verified the significance between analyses using Duncan's multiple range test.

Experiment 2-3. IL-6 Secretion Measurement

As shown in Table 3 below, treatment with LPS alone increased the cytokine IL-6 (interleukin-6) secretion. However, co-treatment with LPS and PEP-1 showed a decrease in the level of the proinflammatory cytokine IL-6 secretion. More importantly, after the treatment with PEP-1, the level of proinflammatory cytokine secretion decreased by more than 70%, which indicates a robust anti-inflammatory effect of PEP-1.

TABLE 3

Cytokine IL-6 production inhibition by PEP-1

| Test sample | | cytokine IL-6 production | |
|---|---|---|---|
| | | % of control | inhibition % |
| | PBS | 0 | — |
| LPS 1 μg/ml | PBS | 100 | 0 |
| | PEP 1 (5 μg/ml) | 28 | 72 |

Experiment 2-4. HMGB1, TNF-α, COX-2 Expression Inhibition

Protein expression level was determined by Western blot analysis. Cells grown in PEP-1 containing medium were washed with PBS, treated with 0.05% trypsin-EDTA, and collected by centrifugation. The collected cells were dissolved in an appropriate volume of lysis buffer. Intracellular debris was pelleted by centrifugation, and equal amount of protein from each sample was separated by SDS-polyacrylamide gel electrophoresis. The separated protein was transferred to nitrocellulose membrane (Schleicher and Schuell, Keene, N.H., USA), then was tested for the antibody specific for each protein. The membrane was incubated with ECL (enhanced chemiluminoesence) solution (Amersham Life Science Corp., Arlington Heights, Ill., USA), exposed to X-ray, and the level of protein expression was analyzed according to the exposure level shown on the X-ray film.

Western blot analysis was performed to determine the inhibitory effect of PEP-1 on the cytokine protein expression. As shown in Table 4 below, stimulation of cells with LPS increased the expression of cytokines; HMGB1, TNF-α and COX. However, if cells were treated with both LPS and PEP-1, the expression level of pro-inflammatory cytokines mentioned above decreased. The result showing the treatment with PEP-1 decreased proinflammatory cytokine levels by more than 70% provide strong evidence supporting the anti-inflammatory effect of PEP-1.

TABLE 4

The measurement of inhibitory effect of PEP-1 on pro-inflammatory cytokine expression level.

| Test sample | | Cytokine Expression Level (band intensity) % of control | | |
|---|---|---|---|---|
| | | HMGB1 | TNF-α | COX-2 |
| | PBS | — | — | — |
| LPS 1 μg/ml | PBS | 100 | 100 | 100 |
| | PEP 1 (5 μg/ml) | 30 | 25 | 22 |

Example 3

Investigation of the Inhibitory Effect of PEP-1 on TNF-α Level in HepG2 Cells Experiment 3-1: Cell Culture PBMC (peripheral blood mononuclear cell) was separated from the blood samples (50 ml) collected from healthy subjects using Ficoll-Paque™ PLUS (GE Healthcare Life Sciences, Piscataway, N.J., USA). PBMCs were then enriched in complete RPMI 1640 medium containing 20% of human serum, followed by transferring to 100 mm polystyrene cell culture plate coated with human serum for 30 mins. After 2 hr incubation at 37° C. and 5% $CO_2$, the monocytes were detached from the bottom of cell culture plate using cold PBS (Phosphate Buffered Saline) (Gibco/Life Technologies, Carlsbad, Calif., USA), and $1 \times 10^5$ cells were cultured in each well of 96-well plate in RPMI 1640 medium (supplemented with penicillin-streptomycin; 100 mg/ml, human serum; 20%) over night.

For Luciferase Analysis, HEK293/null (human embryonic kidney) cells and HEK293/TRL stably expressing TLR2 (toll-like receptor2) obtained from Seoul National University School of Dental Medicine were used. One day before the luciferase experiment, $2.5 \times 10^5$ cells were seeded into each well of 12-well plate and cultured overnight in DMEM (Dulbecco's modified Eagle's medium) medium (supplemented with blasticidin; 10 μg/ml, fetal bovine serum; 10%) (Invitrogen/Life Technologies, Carlsbad, Calif., USA)

Experiment 3-2: Cytokine Assay

To see the effect of PEP-1 on TNF-α level in terms of protein expression level, ELISA (enzyme linked immunosorbent assay) was performed. $1 \times 10^5$ PBMC-derived monocytes were cultured in 96-well plate over night. After then, LPS (lipopolysaccharide; 10 ng/ml, Sigma) was treated for 2 hours, followed by 3 times washes with PBS. OPTI-MEM medium (Invitrogen/Life Technologies, Carlsbad, Calif., USA) was then treated for an hour to induce the starvation, and 4 μM of FITC (Fluorescein Isothiocyanate), FITC-TAT, PEP-1-FITC, and FITC-PEP-1 were treated for 2 hours before measuring the TNF-α level. After culturing, cell soup was collected, and the amount of TNF-α was measured using ELISA kit (R&D, Minneapolis, Minn., USA) as follows:

TNF measurement uses sandwich ELISA method. 100 μl of TNF-α primary antibody was added into each well of pre-coated 96-well plate, and the plate was incubated at 4° C. overnight. On next day, the plate was washed 3 times with 0.5% Tween 20 wash solution for 5 min each, and then 100 μl of each sample and standard solution was added and left at room temperature for 2 hrs. After washing the plate like above, 100 μl of HRP-conjugated secondary antibody was added into each well and left at room temperature for 2 hrs. Again, plate was washed, and avidin/biotin was added for measuring the absorbance. TNF-α level of each sample was quantified using the standard graph calculated from the absorbance of standard solution.

PBMC-derived monocytes were stimulated with endotoxin LPS (10 ng/ml) for 2 hrs, starved for 1 hr using OPTI-MEM, and then 4 μM of FITC, FITC-TAT, PEP 1-FITC and FITC-PEP 1 were treated for 2 hrs. After incubation, TNF-α level was measured with cell culture medium using ELISA. As a result, in case of FITC and FITC-TAT, TNF-α level increased due to LPS (6.2 and 6.7 ng/ml, respectively), but TNF-α level significantly decreased in case of PEP-1-FITC and FITC-PEP-1 (0.17 and 0.25 ng/ml, respectively) and the difference was statistically significant ($P<0.01$) (FIG. 1).

Experiment 3-3: Luciferase Assay

To investigate the role of PEP 1 in inflammatory response, we evaluated NF-κB expression patterns through luciferase analysis. First, we incubated HEK293/null and HEK293/TLR2 (Graduate School of Dentistry, Seoul National University) in a 12-well plate for 24 hours, so that we would get $2.5 \times 10^5$ cells/well. After washing three times with PBS, medium was replaced with OPTI-MEM (Invitrogen/Life Technologies, Carlsbad, Calif., USA) and incubated for 4 hours, and then a mixture of 3 μl lipofectamine (Invitrogen/Life Technologies), NF-κB luciferase and 10 ng renilla luciferase (Promega, Madison, Wis., USA) was added into each well and again incubated for 4 hours. Lipoprotein pam3cys (long/ml, Sigma-Aldrich, St. Louis, Mo., USA) was put into all of the wells except for those of negative control, and FITC (4 μM) and FITC-PEP 1 (4 μM) were treated for 18 hours before it was washed with PBS for three times. We confirmed the activation of NF-κB through TD-20/20 luminometer (Turner designs, Sunnyvale, Calif., USA) after dissolving (lysis) of cells by putting 50 μl of passive lysis buffer—provided by dual-luciferase reporter assay system (Promega)—into each well. Transfection efficacy was confirmed by cotransfection of pCMV-renilla luciferase (Promega), and we analyzed results by calibrating the luciferase values.

Figure 2:
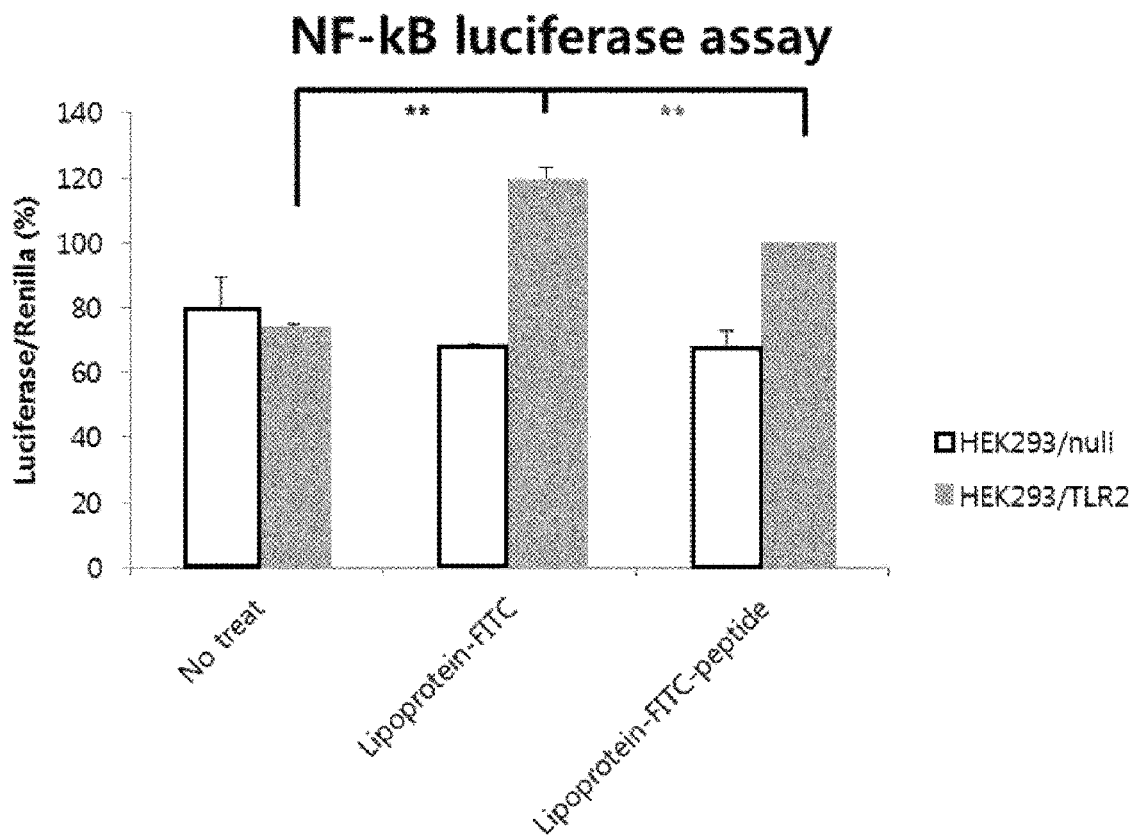
FIG. 2 is a graph which shows the results of performing luciferase analysis from transfecting HEK293/null and HEK293/TLR2 cell lines with NF-κB luciferase, then reacting with lipoprotein (10 ng/ml) and FITC and FITC-PEP-1 (4 μM), and incubating for 18 hours. Results of luciferase were obtained by correction using renilla. (**$P<0.01$. compared to the negative control (No treat) and compared with lipoprotein treated sample.)

After transfecting NF-κB luciferase to HEK293/null and HEK293/TLR2 cell lines, pam3cys, a synthetic lipoprotein, and FITC (4 μM), a negative control were treated together, and pam3cys with FITC-PEP 1 (4 μM) were again treated together to be cultured for 18 hours. The measurement of NF-κB expression patterns by luciferase strength through lysis of cells with passive lysis buffer—provided by dual-luciferase reporter assay system (Promega)-showed that there was no difference in lipoprotein or FITC-PEP-1 treated or non-treated HEK293/null. However, when lipoprotein, an agonist of TLR2, was treated to HEK293/TLR2 cell line, NF-κB expression increased ($P<0.01$) compared to that in untreated, confirming occurrence of inflammatory responses. Also, NF-κB expression increased when FITC-PEP 1 was treated together compared to that in untreated; and expression decreased compared to the negative control in which lipoprotein and FITC were treated together ($P<0.01$) (FIG. 2). Ultimately, we were able to confirm that inflammatory response that can be caused by TLR 2 is reduced when PEP 1 is treated together.

Experiment 3-4: Reanalysis of Peptides that Affect Levels of Cytokines in THP1 Cell Line As a Human acute monocytic leukemia cell line, THP-1 monocyte cell line (American Type Culture Collection (Manassas, Va., USA) was used to reconfirm the effects of PEP 1. Cells were grown at a density of $0.5-7 \times 10^5$ cells/mL in RPMI 1640 containing 10% FBS, 0.05 mM 2-mercaptoethanol, 100 U/ml penicillin, 100 m/mL streptomycin, and maintained at 37° C. under 5% $CO_2$. THP-1 cells were differentiated into macrophages by treating cells with phorbol myristate acetate (PMA) at 100 ng/mL for 24 hr at 37° C. for 24 hr.

All reagents and medium were purchased from Gibco BRL. PMA, LPS and 2-mercaptoethanol were purchased from Sigma (St. Louis, Mo., USA). Peptide RIA was synthesized from Peptron (Daej eon, Republic of Korea). Reverse transcription PCR kit was purchased from Promega (Madison, Wis., USA). $RT^2$ SYBR® Green qPCR (qPCR reagents) Mastermix_reagents and QIAZOL® (lysis reagent) were purchased from QIAGEN (Valencia, Calif., USA).

Following differentiation into macrophages, THP-1 cells were washed two times using complete RPMI 1640 (5 min/wash). Then, cells were treated for 4 hr. with 10 ng/ml LPS and/or 4 μM peptide MA in FBS free RPMI 1640.

Total RNA samples were isolated from peptide-treated THP-1 cells by using Trizol (QIAZOL® (lysis reagent)) reagent and, and cDNA was synthesized by reverse transcriptase PCR using reverse transcription PCR kit from Promega following manufacturer's protocol.

Then, real-Time qPCR was performed using CFX96 (Bio-Rad) instrument with SYBR® Green system (qPCR reagents). Primers used in the experiments are found in Table 5. The PCR cycling conditions were 95° C. for 10 min for activation of HotStart DNA Taq Polymerase, followed by 45 cycles of 95° C. for 10 sec, 55° C. for 30 sec, and 72° C. for 30 sec. All samples were measured in triplicate and differences in gene expression were calculated using the 2-cycle threshold method. All the data were normalized against β actin (housekeeping gene) and presented as means of +/−S.E. from at least three independent experiments.

TABLE 5

Primers used for qRT-PCR analysis.

| SEQ ID | Gene Name | | DNA sequence |
|---|---|---|---|
| 2 | tnf- | (forward) | 5'-CTATCTGGGAGGGGTCTTCC-3' |
| 3 | alpha | (reverse) | 5'-ATGTTCGTCCTGCTCACAGG-3' |
| 4 | beta | (forward) | 5'-GGACAAGCTGAGGAAGATGC-3' |
| 5 | | (reverse) | 5'-TCGTTATCCCATGAGTCGAA-3' |
| 6 | il-6 | (forward) | 5'-AAAAGTCCTGATCCAGTTCCTG-3' |
| 7 | | (reverse) | 5'-TGAGTTGTCATGTCCTGCAG-3' |
| 8 | il-8 | (forward) | 5'-GTGCAGTTTTGCCAAGGAGT-3' |
| 9 | | (reverse) | 5'-AATTTCTGTGTTGGCGCAGT-3' |
| 10 | inos | (forward) | 5'-CACCATCCTGGTGGAACTCT-3' |
| 11 | | (reverse) | 5'-TCCAGGATACCTTGGACCAG-3' |
| 12 | beta | (forward) | 5'-AGAAAATCTGGCACCACACC-3' |
| 13 | actin | (reverse) | 5'-GGGGTGTTGAAGGTCTCAAA-3' |

As shown in FIG. 3, the cytokines involved in the inflammatory responses decreased noticeably by treating with PEP 1.

Example 4

Analysis of Inflammatory Response Induced by Amyloid-β Protein

HMGB1 first undergoes acetylation and translocation to cytoplasm by external stimulation. Then it is secreted out of the cell, therefore serving the role of inflammation-causing cytokine. Because when one has an inflammation due to such activity, HMGB1 protein is secreted from the cell, and patients with inflammatory diseases such as Churg strauss syndrome, rheumatoid arthritis and Sjogren's syndrome will present with elevated serum levels of HMGB1. Hence, if nucleus contains large amount of HMGB1 even when there is a stimulus that causes inflammation, it is suggestive of the fact that HMGB1 is not being secreted out of the cell, which means inflammation is being suppressed.

Experiment 4-1: Analysis of Survival and Proliferation of Neural Stem Cells by Anti-Inflammatory effects of PEP-1

First of all, PEP-1 was prepared according to the manufacturing methods described in Example 1.

Experiment 4-2: Neural Stem Cell Culture and Amyloid-β Toxicity Assessment

After removing the cortex from the head of an embryonic rat that had been pregnant for 13 days, it was cultured for a week with Basic Fibroblast Growth Factor (bFGF) to obtain the neural stem cells. To analyze the effects of the amyloid-β protein on the neural stem cells, the pre-oligomerized amyloid-β protein of concentrations 0 to 40 μM was treated on neural stem cells for 48 hours, then CCK-8 assay, BrdU, and TUNEL assay were used for cytotoxicity assessment (refer from BA Yankner et al, 1990 and KN Dahlgren et al, 2002). We used the same concentration of amyloid-β protein in subsequent experiments after we confirmed that cell survival was reduced to 60% when processed with 20 μM of amyloid-β protein (Refer to FIGS. 4 and 5).

Experiment 4-3: Cell Toxicity Assessment by Treatment with PEP-1

Figure 7:
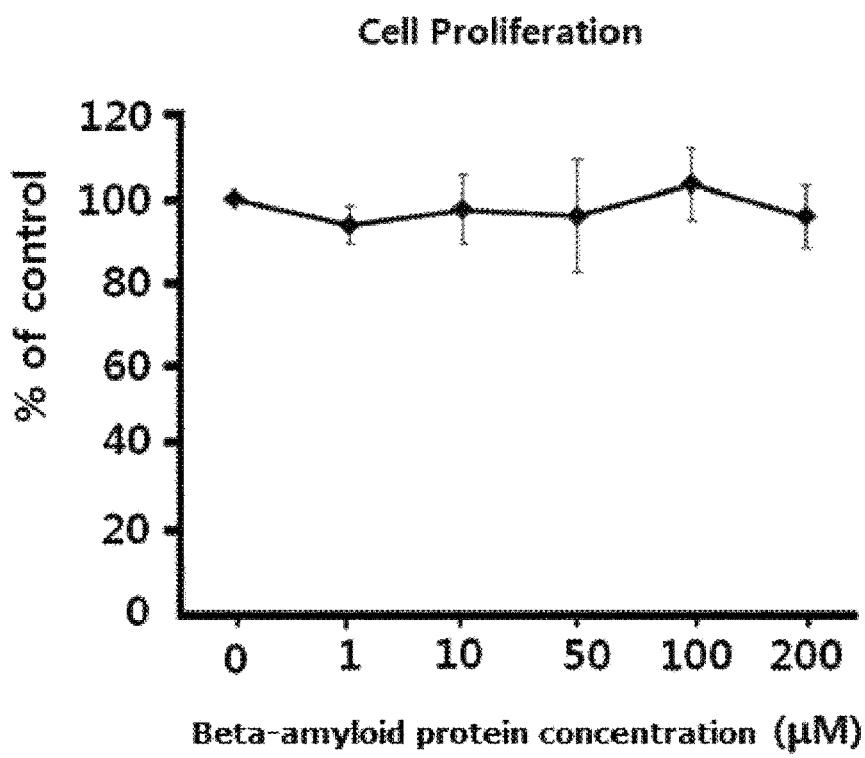
FIG. 7 represents proliferation of neural stem cell treated with 0, 1, 10, 50, 100 and 200 μM of PEP 1.

To evaluate the impact of PEP-1 on the cultured neural stem cells, the neural stem cells were firstly cultured by a well-known method (BA Yankner et al, 1990 and KN Dahlgren et al, 2002). Then, different concentrations (0, 1, 10, 50, 100, 200 μM) of PEP-1 were treated for 48 hours, followed by cell viability and proliferation assessments using MTT assay, BrdU and TUNEL assay. PEP-1's concentrations from 0 to 200 μM appeared stable in the neuronal system since they did not inhibit both survival and proliferation of neural stem cells (Refer to FIGS. 6 and 7).

Experiment 4-4: Cell Toxicity Assessment by Co-Treatment of Amyloid-β Protein and Telomerase Peptide To determine whether PEP 1 has the effect of suppressing the neurotoxicity caused by amyloid-β protein, 20 μM amyloid-β protein and various concentrations of PEP-1 were co-treated for 48 hours. The cell viability and apoptosis were measured using MMT assay, CCK-8 assay, LDH assay and TUNEL assay, and neural stem cell proliferation by BrdU assay.

Figure 8:
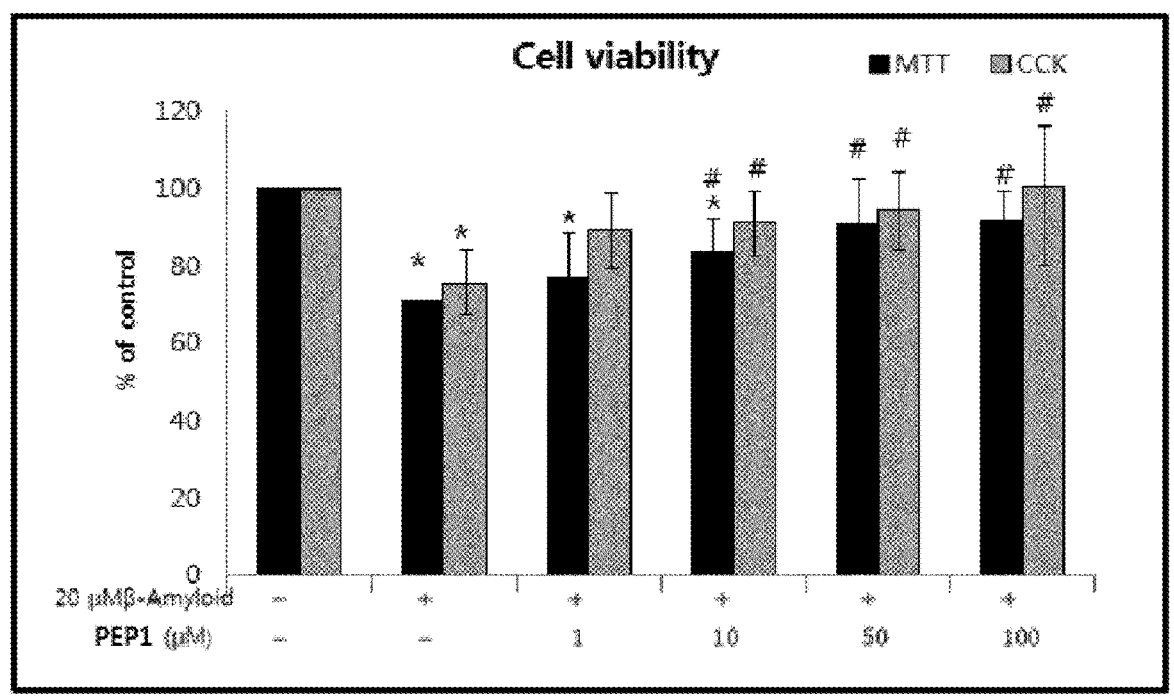
FIG. 8 represents viability of neural stem cell treated with 1, 10, 50 and 100 μM PEP 1; neural stem cells were damaged by 20 μM of amyloid beta protein, and then cell viability was measured after treatment with different concentrations of PEP-1. (Control groups were those untreated with amyloid beta protein and telomerase-based peptides).
Figure 9:
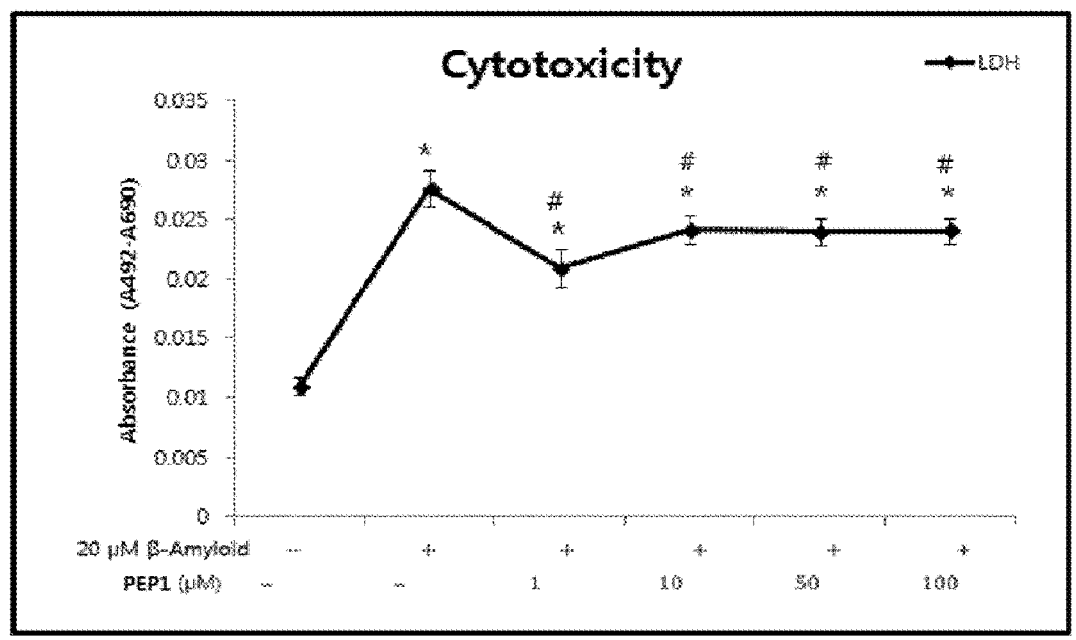
FIG. 9 represents toxicity of neural stem cell treated with 1, 10, 50 and 100 μM PEP 1; neural stem cells were damaged by 20 μM of amyloid beta protein, and then cell toxicity was measured after treatment with different concentrations of PEP-1. (Control groups were those untreated with amyloid beta protein and telomerase-based peptides).

The results of MMT assay and CCK-8 assay confirmed that 10 μM of PEP-1 began to protect neural stem cells from neurotoxicity by amyloid-β, and the most effective protection was provided in 100 μM. (Refer to FIG. 8). LDH assay was carried out for assessment of the degree of cell death as another method, and we confirmed that the increase in cell death by amyloid-β decreased by PEP-1, and efficacy was seen starting at 1 μM concentration (Refer to FIG. 9).

Figure 10:
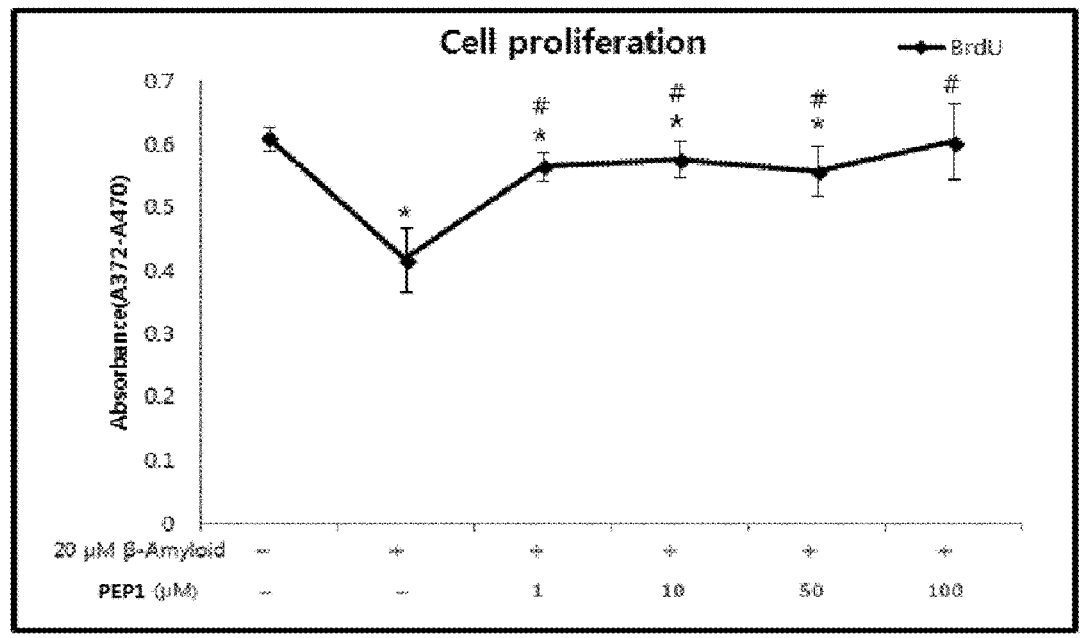
FIG. 10 represents proliferation of neural stem cells treated with 1, 10, 50 and 100 μM PEP 1; neural stem cells were damaged by 20 μM of amyloid beta protein, and then cell proliferation was measured after treatment with different concentrations of PEP-1. (Control groups were those untreated with amyloid beta protein and telomerase-based peptides).

We also confirmed with BrdU assay that the decreased cell proliferation due to amyloid-β protein was restored when processed with PEP-1 (Refer to FIG. 10).

Figure 11:
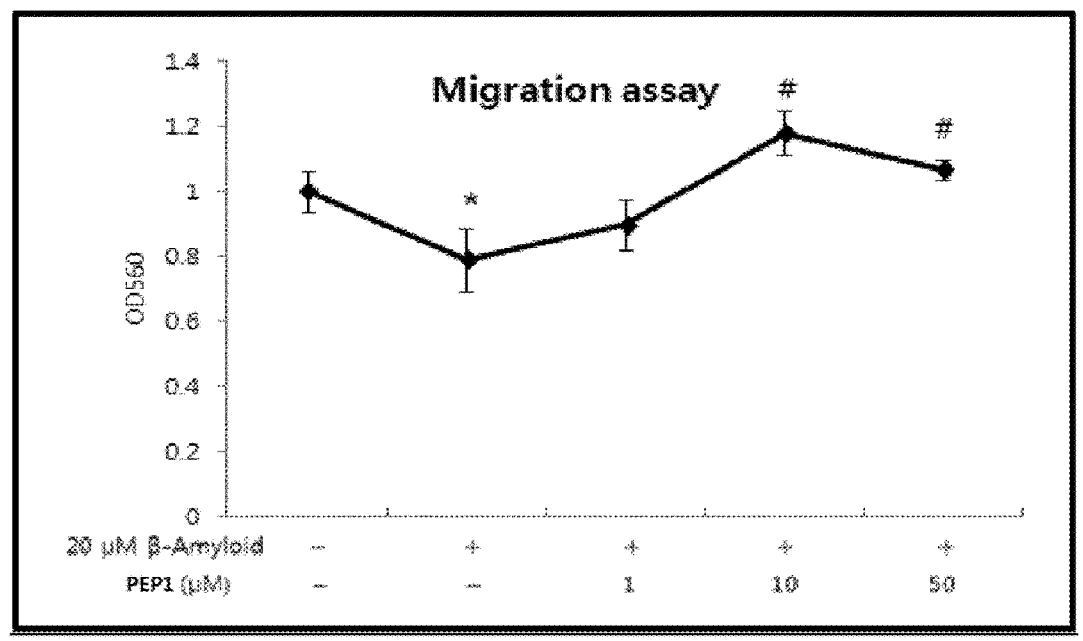
FIG. 11 represents migration of neural stem cells treated with 1, 10, 50 and 100 μM PEP 1; neural stem cells were damaged by 20 μM of amyloid beta protein, and then cell migration was measured after treatment with different concentrations of PEP-1. (Control groups were those untreated with amyloid beta protein and PEP-1).

Cell mobility is a vital matter due to the nature of neural stem cell. According to the experimental results of cell mobility, we confirmed that the decreased cell proliferation due to amyloid-β protein was restored when processed with PEP-1, and that it increased even more when in 10 μM concentration, compared to control. This suggests that in the future clinical trials, processing prior to stem cell transplantation may draw more effective results. (Refer to FIG. 11).

Figure 12:
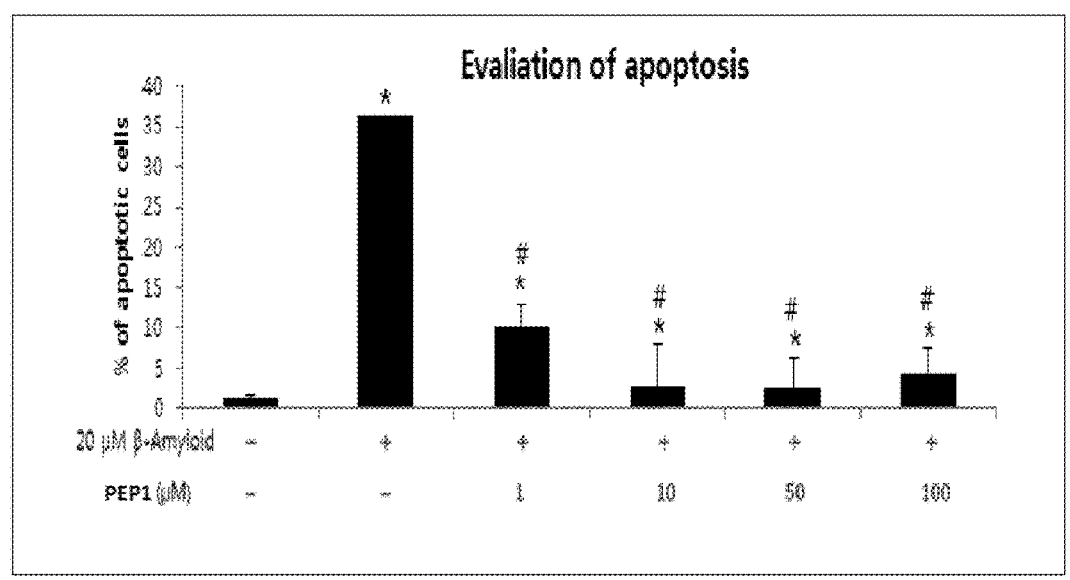
FIG. 12 represents apoptosis of neural stem cells treated with 1, 10, 50 and 100 μM PEP 1; neural stem cells were damaged by 20 μM of amyloid beta protein, and then cell apoptosis was measured after treatment with different concentrations of PEP-1. (Control groups were those untreated with amyloid beta protein and telomerase-based peptides).

To confirm the degree of neuronal stem cells damage, TUNEL assay was performed. Neuronal stem cell death was observed to be significantly increased in 20 μM amyloid-β protein treatment group, and neuronal stem cell death decreased when treated with 1 to 100 μM of PEP 1. (Refer to FIG. 12)

Figure 13:
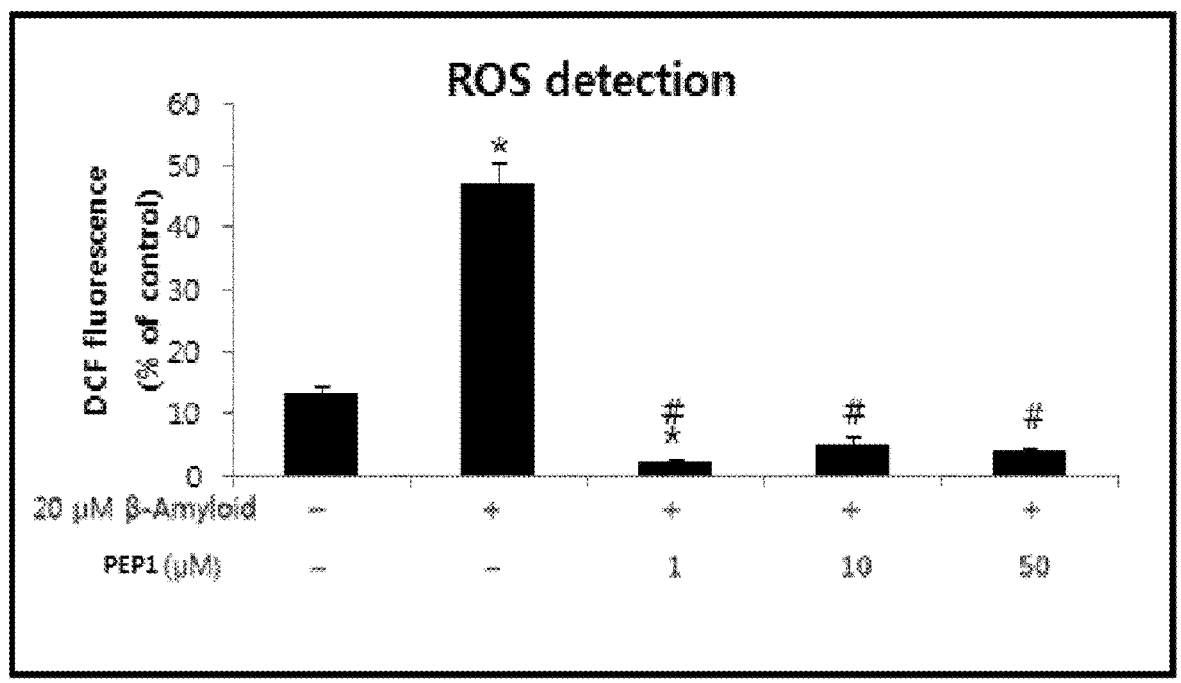
FIG. 13 represents ROS (Reactive Oxygen Species) inhibitory effect of PEP-1 in neural stem cells damaged by amyloid beta peptide; neural stem cells were damaged by 20 μM of amyloid beta protein, and then inhibition of ROS was measured after treatment with different concentrations of PEP-1 (1, 10, 50 and 100 μM). (Control groups were those untreated with amyloid beta protein and PEP-1).

The mechanism of action of PEP-1's protective effect on apoptosis by amyloid-β protein was investigated. First, it was investigated whether PEP-1 is capable of minimizing the oxidative damage caused by amyloid-β protein. Change in generation of reactive oxygen species after treatment with amyloid-β protein and PEP-1 was observed by using DCF-DA staining (Molecular Probes, Eugene, Oreg.). In the group in which reactive oxygen species increased due to 20 μM of amyloid-β protein, the increased reactive oxygen species decreased by PEP-1 treatment (1 μM, 10 μM, 50 μM) (Refer to FIG. 13).

Experiment 4-5: Comparative Analysis of Protein Expression Levels between the Groups Treated With and Without PEP-1

Protein expression level of PEP-1 treated group and untreated group was analyzed by 2D-electrophoresis technique and antibody microarray technique. Prepared 200 μg by extracting proteome from the neural stem cells cultured in Experiment 3-1 of Example 3. In addition, the group in which PEP-1 was not treated was used as the comparison group in the same condition.

2D-electrophoresis was performed using 12% acrylamide gels. First gel electrophoresis was performed at PI 4-10N, using a gel size of 8.5×7 cm. After electrophoresis, it was dyed with Colloidal Coomassie Blue, and then compared expression by using PDQuest software to analyze each spot.

Figure 14:
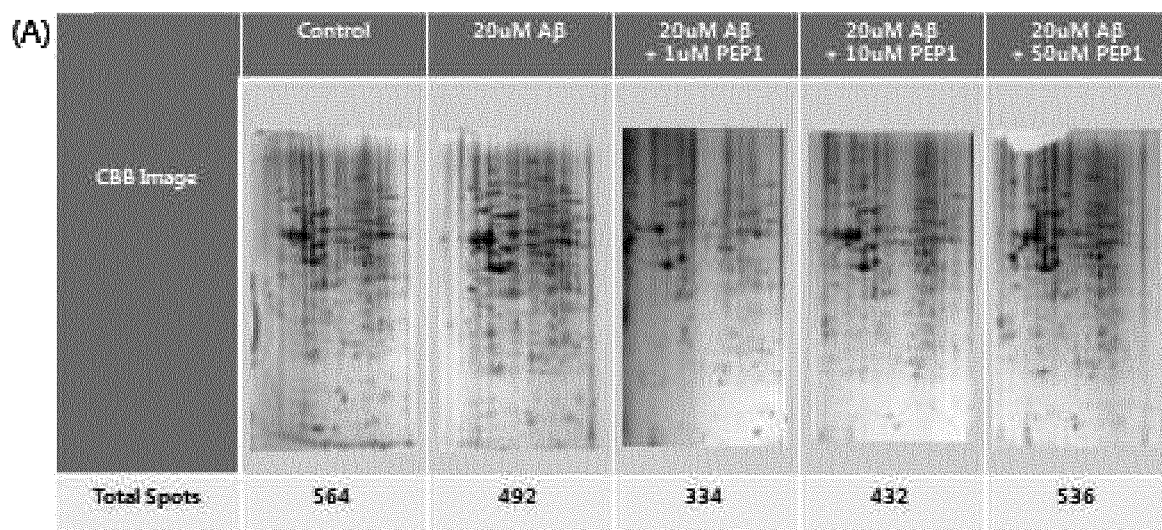
FIG. 14 represents the results of protein expression levels analyzed by (A) 2D-eletrophoresis and (B) Antibody Array; neural stem cells were damaged by 20 μM of amyloid beta protein, and then protein expression level was measured after treatment with different concentrations of PEP-1 (1, 10 and 50 μM). (Control groups were those untreated with amyloid beta protein and PEP-1).
Figure 14:
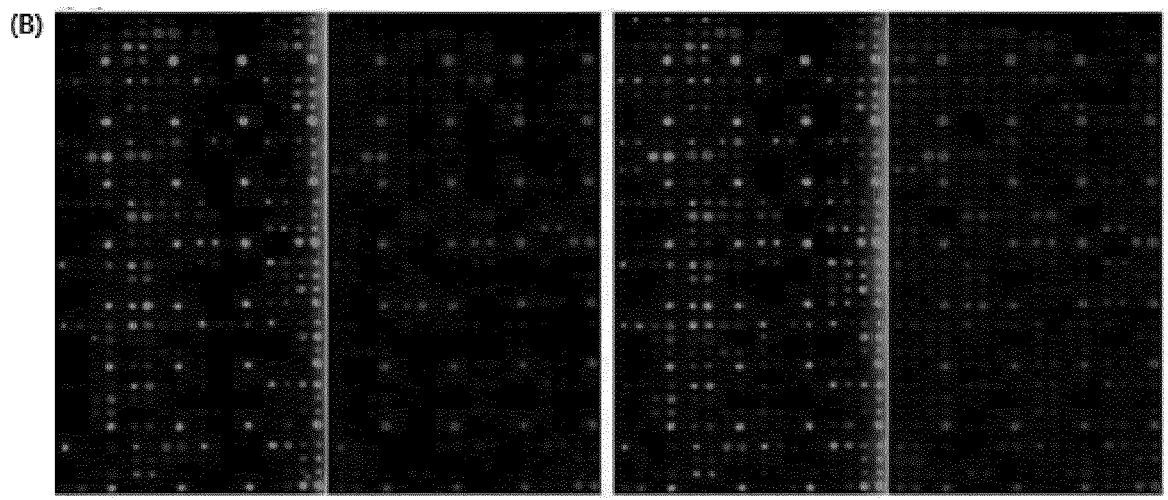

Difference in the expression levels of more than 1.5 times was identified using MALDI-TOF MS (Matrix Desoprtion/Iionization Time of Flight Mass Spectromestry). Among these, proteins correlated with inflammation-related signaling, such as i-NOS and HMGB-1 were identified (Refer to Table 6). The changes in protein expression levels either increased or decreased by 1.5 times by amyloid-β protein, but it was confirmed that expression level was regulated close to that of negative control when PEP-1 was added (Refer to FIG. 14).

Antibody microarray was carried out by using cell signaling kit (CSAA1, PANORAMA' Ab Microarray Cell Signaling kit (proteomics tool that measures the relative level of protein expression)), array slides were scanned by GENEPIX® Personal 4100A scanner (Molecular Devices) and the data were analyzed by GENEPIX® Pro 5.0 (Molecular Devices).

The Table 6 below is an analysis of expression levels of proteins associated with inflammation by 2D electrophoresis technique. The control group represents protein expression level of cells that were not treated with neither amyloid-β protein nor PEP-1. It shows increased or decreased multiple of protein expression based on the control group's expression level.

We confirmed with the results of analysis that like the suggested in Table 6 below, inflammation related protein over-expression or under-expression was controlled by PEP-1; the protein expression level was close to that of negative control group.

TABLE 6

| Protein | Negative Control | 20 μg β-amyloid treated group (fold) | 20 μg β-amyloid + PEP 1 treated group (fold) |
|---|---|---|---|
| HSP 70 | 1.0 | −2.3 | 1.2 |
| HSP 90 | 1.0 | −1.8 | 1.0 |
| HMGB1 | 1.0 | −1.5 | 2.8 |
| GADD 153 | 1.0 | 1.6 | 1.2 |
| i-NOS | 1.0 | 1.9 | −1.1 |
| e-NOS | 1.0 | 1.9 | −1.1 |
| Pyk2 | 1.0 | 2.0 | 1.2 |
| MAP Kinase | 1.0 | 2.2 | 1.0 |

Phosphatidylinositol 3-kinase (PI3K)/AKT signaling pathway serves a crucial role in the growth and survival of neuronal stem cells. PI3K pathway is activated by growth factors and regulatory factors, and is involved in the normal regulation of neuronal stem cell growth and survival. AKT signaling pathways disable several pro-apoptotic factors, including a well-known apoptotic signaling molecule, GSK3β.

Figure 15:
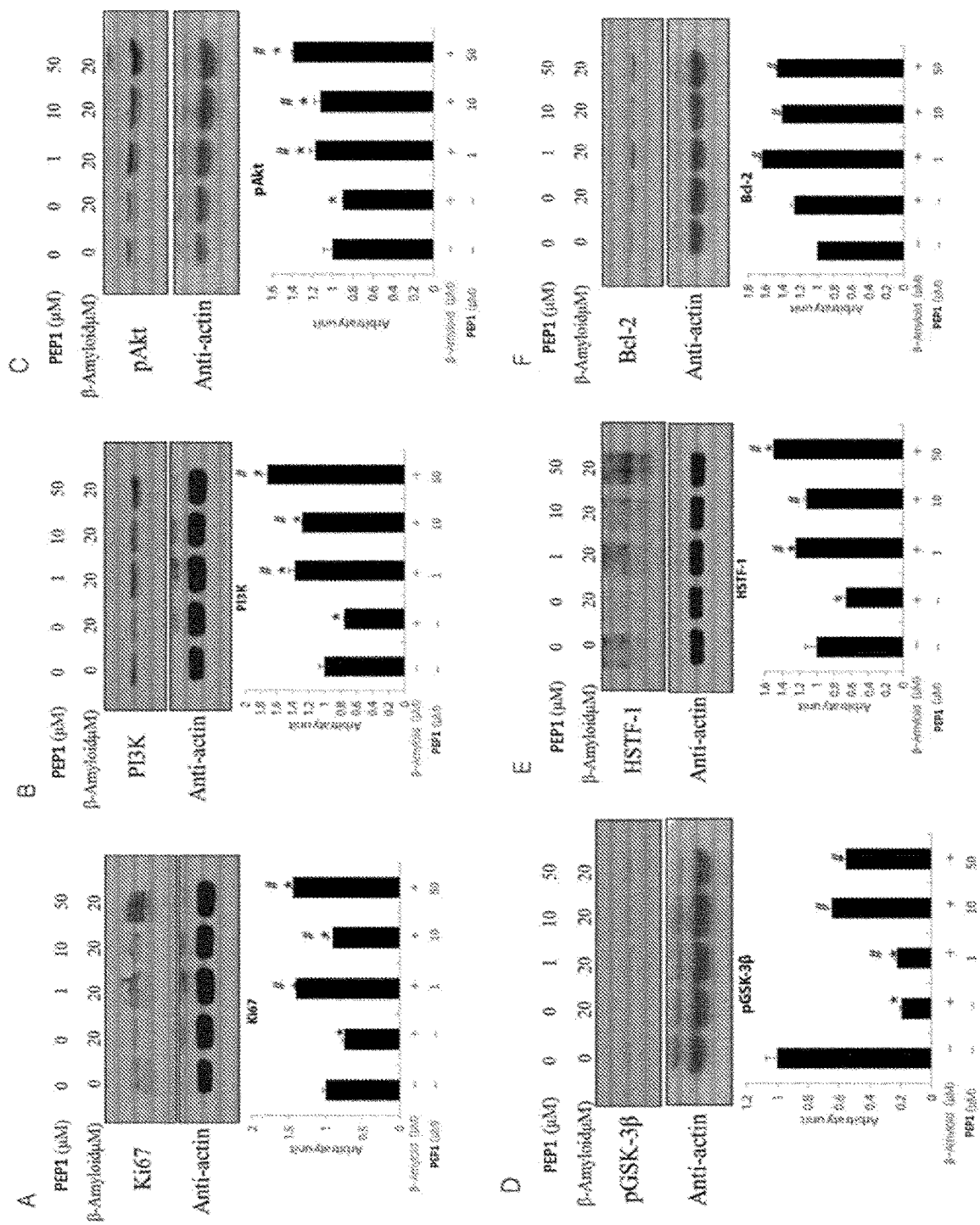
FIG. 15 represents the results of western blot showing the expression level of inflammation-related proteins: neural stem cells were damaged by 20 μM of amyloid beta protein, and then cells were treated with different concentrations of PEP-1 (1, 10 and 50 μM).
Figure 15:
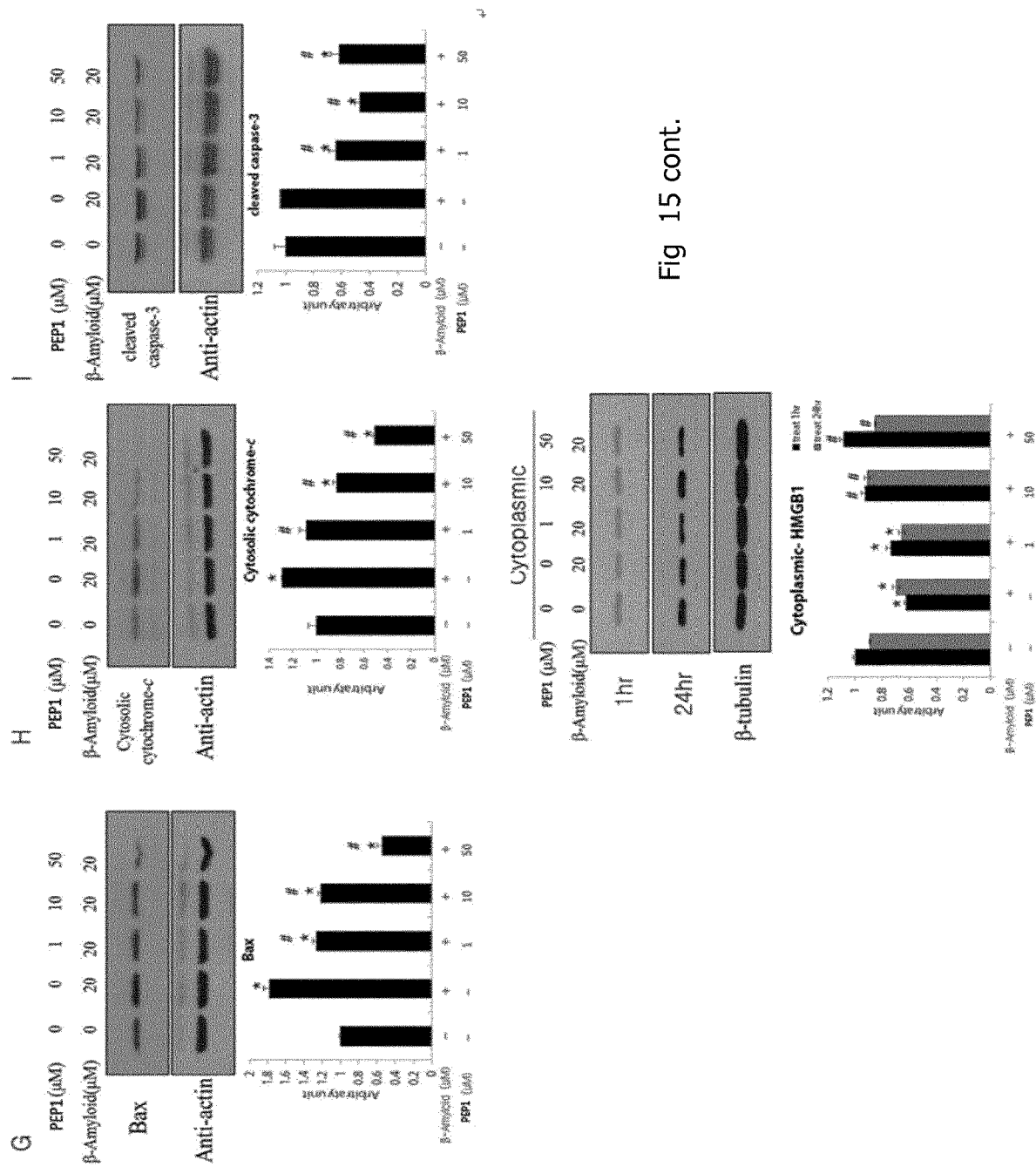

To further investigate the anti-inflammatory effects of PEP-1, we performed Western blot on HMGB1, since it showed a major change in protein analysis. As a result, the processing of the PEP-1 increased the protein expression levels in anti-apoptotic proteins such as Ki67, pAKT, PI3K, HSTF-1 and Bcl-2, and decreased the protein expression levels of apoptotic signals such as Bax, GSK3β, Cytochrom-c, caspase-3 (Refer to FIG. 15).

HMGB1, a non-histone structure protein that binds to DNA, serves diverse roles within a cell; such as stabilizing nucleosome structure and regulating gene expression. As one of the inflammation-causing substance that is excreted in the late phase of inflammatory response, it is excreted by macrophages and monocytes when inflammation is stimulated, but when neuron is significantly damaged and leads to cell necrosis, it will be excreted out of the cell, causing an intense inflammatory response. The increase of HMGB1 by PEP-1 treatment after the decrease by amyloid-β treatment in the cytoplasm of the nerve cells reflects the fact that PEP-1 inhibits secretion of HMGB1 out of the cell caused by neuron cell death; therefore suggesting that PEP-1 has powerful anti-inflammatory effects (Refer to FIG. 15).

Figure 16:
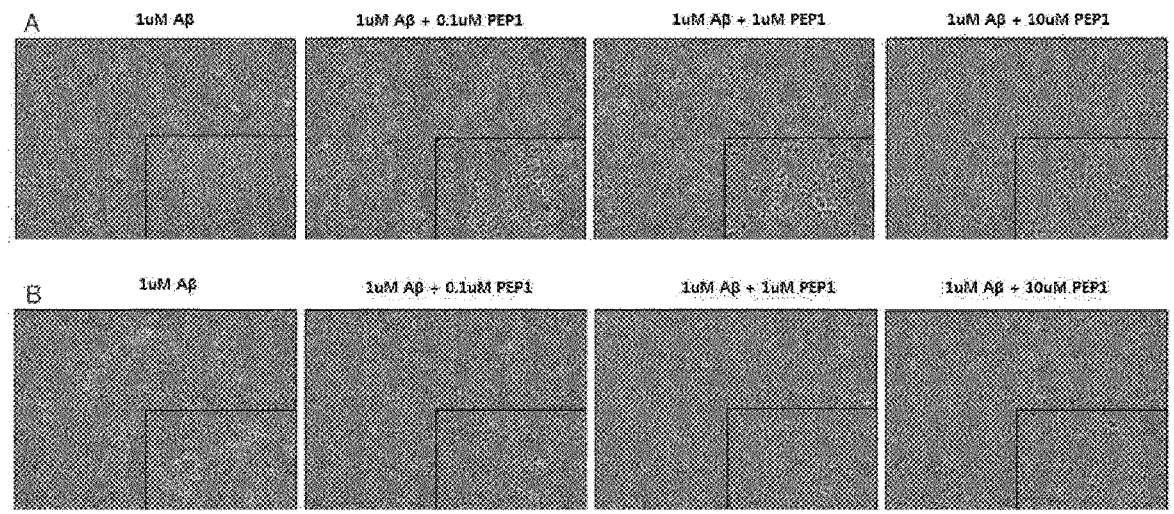
FIG. 16 represents the inhibitory effect of PEP 1 on amyloid beta protein aggregation; (A) shows the reduced oligomerization of amyloid beta proteins when co-treated with 1 μM amyloid beta protein and PEP 1 (0.1, 1 and 10 μM). (B) shows the case when PEP-1 was treated on the amyloid-β protein that was already induced for aggregation.

In addition, we investigated the response of PEP-1 to the amyloid-β aggregation. Aggregation of protein was inhibited when treated with PEP-1 (Refer to FIG. 16(A)) in induction of aggregation of amyloid-β, and protein underwent degradation when PEP-1 was treated on the amyloid-β protein that was already induced for aggregation (Refer to FIG. 16(B)).

Figure 17:
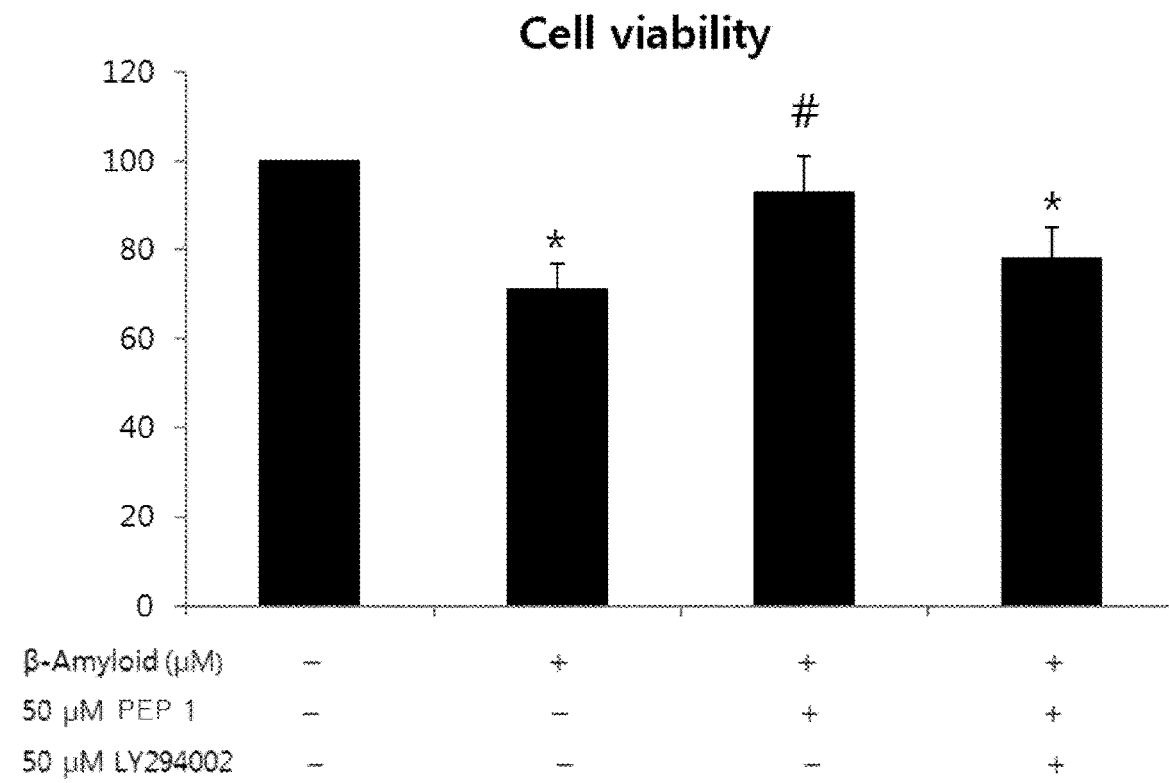
FIG. 17 represents the effect of PI3K-inhibitor, LY294002 on the cell viability treated with PEP 1. The increased cell viability after treating with PEP 1 decreased when treated with LY294002.

In the mechanism of action of PEP-1, we have previously confirmed the increase in cell survival signaling and decrease in apoptosis signaling of PI3K. To investigate whether these effects are direct or indirect, we treated PI3K-inhibitor, LY294002 (Promega). As a result, the increased cell viability after treating with PEP 1 decreased when treated with LY294002. Thus, we can conclude that PI3K is directly associated with PEP 1's neuroprotective effect (Refer to FIG. 17).

PEP-1 inhibits apoptosis of neural stem cells by amyloid-β protein. Also, the improvement of cell mobility of neural stem cells was confirmed, therefore suggesting a variety of possibilities in clinical application. The inhibition effects from neurotoxicity caused by beta-amyloid protein was verified by the anti-inflammatory effect of the mechanism of action of PEP 1, increased survival factors of neuro stem cells and decreased apoptotic factors, especially activation of PI3K signaling pathway and antioxidant effects.

Example 5 qPCR array

Materials and Methods

THP-1 Cell Culture

THP-1 cells (human monocytic leukemia derived cell line) were purchased from ATCC (American Type Culture Collection, Manassas, Va., USA) and cultured in RPMI-1640 (Life technologies, Carlsbad, Calif., USA) medium supplemented with 10% FBS (Life technologies), 1% penicillin/streptomycin (Life technologies), and 0.05 mM 2-mercaptoethanol (Sigma-Aldrich, St. Louis, Mo., USA) at 37° C. in 5% $CO_2$. THP-1 cells that normally grow in suspension were differentiated into an adherent macrophage-like phenotype in differentiation medium (complete growth medium containing 100 ng/mL phorbol 12-myristate 13-acetate (PMA, Sigma-Aldrich)) for 24 hr. For differentiation, THP-1 cells ($3\times10^6$ cells/plate, ~95% confluency) were seeded into 10-cm tissue culture plates and incubated in differentiation medium.

Treatment of THP-1 Cells with Anti-Inflammatory Peptide, PEP-1

Following differentiation, the macrophage-like THP-1 cells were washed twice using complete growth medium. Then, cells were treated with 10 ng/mL lipopolysaccharide (Sigma-Aldrich) and/or 4 µM PEP-1 for 4 h at 37° C.

RNA Isolation and cDNA Synthesis from THP-1 Cells

Total RNA was extracted and purified using RNeasy mini kit from Qiagen (Valencia, Calif., USA) following manufacturer's protocol. cDNAs were synthesized by reverse transcription using Reverse Transcription System from Promega (Madison, Wis., USA) according to the manufacturer's protocol.

PCR Arrays

Then, cDNA samples from THP-1 cells were used as template for real-time quantitative PCR (qPCR) analysis. For qPCR analysis, $RT^2$ Profiler PCR Array kits were purchased from SABiosciences/Qiagen (Valencia, Calif., USA). Four different PCR array kits analyzing separate signaling pathways used in the experiment are as follows: human signal transduction pathway finder, human inflammatory cytokines & receptors, human transcription factors, human NF-κB signaling pathway. PCR was performed with SYBR® Green qPCR system (qPCR reagents, Qiagen) using a Bio-Rad (Hercules, Calif., USA) CFX 96 real-time PCR instrument. Thermocycling conditions were: 95° C. for 10 sec; 55° C. for 30 sec; 95° C. for 10 min; 95° C. for 10 sec, 55° C. for 30 sec, and 72° C. for 30 sec for 50 amplification cycles. Data represents the average value from three independent experiments, and % decrease was determined by the target gene expression in LPS treated samples vs. LPS+PEP-1 treated samples. Among 336 genes analyzed, only those showing statistically significant ($p<0.05$, student's t-test) % decrease were shown in table 7.

Results

TABLE 7

PEP-1 inhibits the genes shown in the table above (*, NF-κB target genes containing consensus NF-κB binding sites in the promoter region).

| Signalling pathway | Gene | % Decrease by PEP 1 (LPS + PEP-1/LPS), $p < 0.05$ |
|---|---|---|
|  | TNFα* | ↓↓34% |
|  | IL10* | ↓↓32% |
|  | IL1Ra* | ↓20% |
|  | IL17C | ↓↓35% |
|  | G-CSF* | ↓↓↓48% |
|  | GM-CSF* | ↓↓29% |
|  | CCL4/MIP1β* | ↓22% |
|  | CCL26/MIP4α | ↓↓↓42% |
| TNF Receptor Family | TNFR11β | ↓↓↓38% |
|  | CD40Ligand | ↓18% |
| Lipid biosynthesis | ACSL5 (acyl-coA synthase) | ↓17% |
| Apoptosis | BCL10 | ↓↓32% |
| NFκB | IκBα | ↓↓27% |

PEP-1 inhibited transcription of genes shown in Table 7 with THE % inhibition calculated as the ratio in the level of transcription between LPS treated vs. LPS+PEP-1-treated samples (THP-1 cells). Among the 336 genes analyzed, only the 13 genes in Table 7 showed statistically significant decrease following PEP-1 treatment. Those genes can be grouped into different functional categories, which include chemokines & cytokines, TNFα receptor signaling, lipid metabolism, apoptosis, and NF-κB signaling. More importantly, genes in the chemokines & cytokines category have been known as NF-κB target genes, having NF-κB consensus DNA-binding sites in their promoter regions. Taken together, data from PCR arrays support that PEP-1 may exert anti-inflammatory effects by modulating the master regulator of inflammation NF-κB, and by doing so PEP-1 can be used as anti-inflammatory therapeutic agents in a wide range of inflammatory diseases.

---

The invention claimed is:

1. A method for treating a urogenital disorder comprising administering to a subject in need thereof a composition comprising the isolated peptide of SEQ ID NO: 1.

2. The method according to claim 1, wherein the inflammatory disease urogenital disorder is selected from the group consisting of epididymitis, vaginitis, prostatitis, and urethritis.

3. The method of claim 1, wherein the composition is administered through oral, rectal, transdermal, intravenous, intramuscular, intraperitoneal, in the bone marrow, epidural, or subcutaneous means.

4. The method of claim 1, wherein the composition comprises 0.1 µg/mg to 1 mg/mg of the isolated peptide.

5. The method according to claim 1, wherein the peptide is administered in a single dose at a concentration of 0.1 µg/kg to 1.0 g/kg.

6. The method according to claim 1, wherein the peptide is administered in a single dose at a concentration of 1 µg/kg to 10 mg/kg.

7. The method according to claim 1, wherein the peptide is administered 1 to 3 times a day.

8. The method of claim 1, wherein the peptide is administered at a daily dose of 0.1 µg/kg to 1.0 g/kg.

9. The method of claim 8, wherein the peptide is administered 1 to 3 times daily.

* * * * *

UNITED STATES PATENT AND TRADEMARK OFFICE
CERTIFICATE OF CORRECTION

Page 1 of 1

PATENT NO. : 10,960,056 B2
APPLICATION NO. : 16/025352
DATED : March 30, 2021
INVENTOR(S) : Sang Jae Kim et al.

It is certified that error appears in the above-identified patent and that said Letters Patent is hereby corrected as shown below:

In the Claims

Column 29 Lines 56-57 Claim 2, replace "inflam-matory disease urogenital disorder" with --urogenital disorder--.

Signed and Sealed this
Eighth Day of June, 2021

Drew Hirshfeld
*Performing the Functions and Duties of the
Under Secretary of Commerce for Intellectual Property and
Director of the United States Patent and Trademark Office*